US009138569B2

(12) United States Patent
Edgren et al.

(10) Patent No.: US 9,138,569 B2
(45) Date of Patent: Sep. 22, 2015

(54) DEVICES AND METHODS FOR DILATING A PARANASAL SINUS OPENING AND FOR TREATING SINUSITIS

(71) Applicant: SinuSys Corporation, Palo Alto, CA (US)

(72) Inventors: David E. Edgren, Los Altos, CA (US); William Jason Fox, San Carlos, CA (US); William L. Gould, Fallbrook, CA (US); Jerome E. Hester, Menlo Park, CA (US); Bradley F. Marple, Dallas, TX (US); Curtis Leslie Rieser, San Jose, CA (US); Thomas A. Schreck, Portola Valley, CA (US)

(73) Assignee: SinuSys Corporation, Palo Alto, CA (US)

( * ) Notice: Subject to any disclaimer, the term of this patent is extended or adjusted under 35 U.S.C. 154(b) by 475 days.

(21) Appl. No.: 13/777,748

(22) Filed: Feb. 26, 2013

(65) Prior Publication Data

US 2013/0231693 A1 Sep. 5, 2013

Related U.S. Application Data

(60) Provisional application No. 61/756,877, filed on Jan. 25, 2013, provisional application No. 61/605,000, filed on Feb. 29, 2012.

(51) Int. Cl.
*A61M 29/00* (2006.01)
*A61M 29/02* (2006.01)
*A61F 2/00* (2006.01)
*A61B 17/12* (2006.01)
*A61F 2/04* (2013.01)
*A61F 2/18* (2006.01)
*A61M 31/00* (2006.01)

(52) U.S. Cl.
CPC .......... *A61M 29/02* (2013.01); *A61B 17/12022* (2013.01); *A61B 17/12104* (2013.01); *A61F 2/0095* (2013.01); *A61F 2/04* (2013.01); *A61F 2/186* (2013.01); *A61M 31/002* (2013.01); *A61M 2209/06* (2013.01)

(58) Field of Classification Search
CPC ....... A61M 29/02; A61M 29/00; A61F 2/186; A61F 2/18; A61B 17/12022; A61B 17/12099; A61B 17/12104
See application file for complete search history.

(56) References Cited

U.S. PATENT DOCUMENTS

| | | | |
|---|---|---|---|
| 3,625,351 A * | 12/1971 | Eisenberg | 206/484 |
| 3,732,865 A | 5/1973 | Higuchi et al. | |
| 3,760,805 A | 9/1973 | Higuchi | |
| 3,760,984 A | 9/1973 | Theeuwes | |

(Continued)

FOREIGN PATENT DOCUMENTS

| | | |
|---|---|---|
| EP | 0923912 | 6/1999 |
| JP | AH4-215768 | 2/1994 |

(Continued)

*Primary Examiner* — Jonathan W Miles
(74) *Attorney, Agent, or Firm* — Rudy J. Ng; Carol L. Francis; Bozicevic, Field & Francis LLP

(57) ABSTRACT

Medical devices which are adapted to be inserted into a patient for a limited period of time using minimally invasive insertion procedures for dilating a stenotic opening, such as a stenotic sinus opening, are provided. The devices and methods can be used for treating sinusitis and other nasal and/or sinus disorders.

12 Claims, 14 Drawing Sheets

(56) References Cited

U.S. PATENT DOCUMENTS

| | | | |
|---|---|---|---|
| 3,786,813 A | 1/1974 | Michaels | |
| 3,845,770 A | 11/1974 | Theeuwes et al. | |
| 4,014,334 A | 3/1977 | Theeuwes et al. | |
| 4,142,526 A | 3/1979 | Zaffaroni et al. | |
| 4,203,440 A | 5/1980 | Theeuwes | |
| 4,203,441 A | 5/1980 | Theeuwes | |
| 4,449,983 A | 5/1984 | Cortese | |
| 4,455,143 A | 6/1984 | Theeuwes | |
| 4,467,806 A | 8/1984 | Bhiwandiwala et al. | |
| 4,663,148 A | 5/1987 | Eckenhoff et al. | |
| 5,160,743 A | 11/1992 | Edgren et al. | |
| 5,234,456 A | 8/1993 | Silvestrini | |
| 5,246,455 A | 9/1993 | Shikani | |
| 5,258,042 A * | 11/1993 | Mehta | 600/36 |
| 5,336,163 A | 8/1994 | DeMane et al. | |
| 5,413,572 A | 5/1995 | Wong et al. | |
| 5,423,745 A | 6/1995 | Todd et al. | |
| 5,464,450 A | 11/1995 | Buscemi et al. | |
| 5,498,255 A | 3/1996 | Wong | |
| 5,499,994 A | 3/1996 | Tihon et al. | |
| 5,500,013 A | 3/1996 | Buscemi et al. | |
| 5,547,378 A | 8/1996 | Linkow | |
| 5,674,241 A | 10/1997 | Bley et al. | |
| 5,693,065 A | 12/1997 | Rains, III | |
| 5,713,855 A | 2/1998 | Shippert | |
| 5,728,396 A | 3/1998 | Peery et al. | |
| 6,123,697 A | 9/2000 | Shippert | |
| 6,224,907 B1 | 5/2001 | Davar et al. | |
| 6,270,787 B1 | 8/2001 | Ayer | |
| 6,336,496 B1 | 1/2002 | Asai et al. | |
| 6,387,124 B1 | 5/2002 | Buscemi et al. | |
| 6,455,065 B1 | 9/2002 | Hymes | |
| 6,648,873 B2 | 11/2003 | Arenberg et al. | |
| 6,753,011 B2 | 6/2004 | Faour | |
| 6,976,983 B2 | 12/2005 | Russell | |
| 7,014,636 B2 | 3/2006 | Gilbert | |
| 7,074,423 B2 | 7/2006 | Fereira et al. | |
| 7,108,684 B2 | 9/2006 | Farnan | |
| 7,108,762 B2 | 9/2006 | Russell | |
| 7,211,076 B2 | 5/2007 | Russell | |
| 7,235,068 B2 | 6/2007 | Theeuwes et al. | |
| 7,235,099 B1 | 6/2007 | Duncavage et al. | |
| 7,241,457 B2 | 7/2007 | Chen et al. | |
| 7,361,168 B2 | 4/2008 | Makower et al. | |
| 7,410,480 B2 | 8/2008 | Muni et al. | |
| 7,419,497 B2 | 9/2008 | Muni et al. | |
| 7,462,175 B2 | 12/2008 | Chang et al. | |
| 7,500,971 B2 | 3/2009 | Chang et al. | |
| 7,520,876 B2 | 4/2009 | Ressemann et al. | |
| 7,544,192 B2 | 6/2009 | Eaton et al. | |
| 7,591,830 B2 | 9/2009 | Rutter | |
| 7,645,272 B2 | 1/2010 | Chang et al. | |
| 7,654,997 B2 | 2/2010 | Makower et al. | |
| 7,678,099 B2 | 3/2010 | Ressemann et al. | |
| 7,678,103 B2 | 3/2010 | Russell | |
| 7,740,642 B2 | 6/2010 | Becker | |
| 7,740,643 B2 | 6/2010 | Maryanka | |
| 2002/0004060 A1 | 1/2002 | Heublein et al. | |
| 2002/0088723 A1 | 7/2002 | Lowry et al. | |
| 2002/0120276 A1* | 8/2002 | Greene et al. | 606/108 |
| 2003/0171773 A1* | 9/2003 | Carrison | 606/213 |
| 2004/0064150 A1 | 4/2004 | Becker | |
| 2004/0073299 A1 | 4/2004 | Hudson et al. | |
| 2004/0098095 A1 | 5/2004 | Burnside et al. | |
| 2004/0098108 A1 | 5/2004 | Harder et al. | |
| 2004/0116958 A1 | 6/2004 | Gopferich et al. | |
| 2004/0127871 A1* | 7/2004 | Odorzynski et al. | 604/378 |
| 2004/0243214 A1 | 12/2004 | Farrell | |
| 2004/0267241 A1 | 12/2004 | Russell | |
| 2005/0054999 A1* | 3/2005 | Morman et al. | 604/367 |
| 2005/0149173 A1* | 7/2005 | Hunter et al. | 623/1.42 |
| 2005/0165379 A1* | 7/2005 | Mawad | 604/500 |
| 2005/0240147 A1 | 10/2005 | Makower et al. | |
| 2005/0245906 A1* | 11/2005 | Makower et al. | 604/891.1 |
| 2005/0268573 A1 | 12/2005 | Yan | |
| 2005/0278012 A1 | 12/2005 | Vonderwalde | |
| 2006/0047247 A1 | 3/2006 | Anders | |
| 2006/0063973 A1 | 3/2006 | Makower et al. | |
| 2006/0106361 A1 | 5/2006 | Muni et al. | |
| 2006/0276831 A1* | 12/2006 | Porter et al. | 606/200 |
| 2007/0073269 A1 | 3/2007 | Becker | |
| 2007/0084144 A1 | 4/2007 | Labrecque et al. | |
| 2007/0106233 A1* | 5/2007 | Huang et al. | 604/271 |
| 2007/0129751 A1 | 6/2007 | Muni et al. | |
| 2007/0160647 A1 | 7/2007 | Pritchard et al. | |
| 2007/0233036 A1 | 10/2007 | Mandpe | |
| 2007/0244562 A1 | 10/2007 | Conner et al. | |
| 2007/0250105 A1 | 10/2007 | Ressemann et al. | |
| 2007/0269385 A1 | 11/2007 | Yun et al. | |
| 2008/0044553 A1 | 2/2008 | Freeman et al. | |
| 2008/0082045 A1 | 4/2008 | Goldfarb et al. | |
| 2008/0097468 A1 | 4/2008 | Adams et al. | |
| 2008/0125805 A1 | 5/2008 | Mische | |
| 2008/0243140 A1 | 10/2008 | Gopferich et al. | |
| 2008/0292255 A1 | 11/2008 | Stevens et al. | |
| 2009/0036968 A1 | 2/2009 | Hepworth et al. | |
| 2009/0098184 A1 | 4/2009 | Govil et al. | |
| 2009/0125046 A1 | 5/2009 | Becker | |
| 2009/0187098 A1* | 7/2009 | Makower et al. | 600/424 |
| 2009/0220571 A1 | 9/2009 | Eaton et al. | |
| 2009/0264976 A1 | 10/2009 | Nagasrinivasa | |
| 2009/0312745 A1 | 12/2009 | Goldfarb et al. | |
| 2009/0314676 A1 | 12/2009 | Peck et al. | |
| 2010/0030113 A1 | 2/2010 | Morriss et al. | |
| 2010/0076269 A1 | 3/2010 | Makower et al. | |
| 2010/0099946 A1 | 4/2010 | Jenkins et al. | |
| 2010/0100116 A1* | 4/2010 | Brister et al. | 606/192 |
| 2010/0106255 A1 | 4/2010 | Dubin | |
| 2010/0155282 A1 | 6/2010 | Govil et al. | |
| 2010/0198191 A1 | 8/2010 | Clifford et al. | |
| 2010/0305603 A1* | 12/2010 | Nielsen et al. | 606/194 |
| 2010/0312101 A1 | 12/2010 | Drontle et al. | |
| 2010/0312338 A1 | 12/2010 | Gonzales et al. | |
| 2011/0004057 A1 | 1/2011 | Goldfarb et al. | |
| 2011/0021975 A1 | 1/2011 | Covello | |
| 2012/0053404 A1 | 3/2012 | Schreck et al. | |
| 2012/0053567 A1 | 3/2012 | Schreck et al. | |
| 2012/0116350 A1 | 5/2012 | Strauss et al. | |
| 2012/0261290 A1 | 10/2012 | Limjaroen et al. | |
| 2013/0138132 A1 | 5/2013 | Phee et al. | |
| 2013/0253564 A1 | 9/2013 | Edgren et al. | |
| 2013/0253567 A1 | 9/2013 | Edgren et al. | |
| 2013/0261550 A1 | 10/2013 | Edgren et al. | |
| 2013/0267987 A1 | 10/2013 | Edgren et al. | |
| 2014/0031852 A1 | 1/2014 | Edgren et al. | |
| 2014/0358177 A1 | 12/2014 | Schreck et al. | |
| 2015/0065810 A1 | 3/2015 | Edgren et al. | |

FOREIGN PATENT DOCUMENTS

| | | |
|---|---|---|
| JP | AH5-76602 | 8/1994 |
| WO | 9503848 | 2/1995 |
| WO | 9829148 | 7/1998 |
| WO | 9962430 | 12/1999 |
| WO | 0247558 | 6/2002 |
| WO | 2005117755 | 12/2005 |
| WO | 2006034008 | 3/2006 |
| WO | 2006020180 | 6/2006 |
| WO | 2007054108 | 5/2007 |
| WO | 2008008389 | 1/2008 |
| WO | 2009018248 | 2/2009 |
| WO | 2010033629 | 3/2010 |

* cited by examiner

DEVICES AND METHODS FOR DILATING A PARANASAL SINUS OPENING AND FOR TREATING SINUSITIS

CROSS-REFERENCE TO RELATED APPLICATIONS

This application claims priority benefit of U.S. Provisional Application Ser. No. 61/605,000, filed on Feb. 29, 2012 and U.S. Provisional Application Ser. No. 61/756,877, filed on Jan. 25, 2013, the disclosure of each of which application is herein incorporated by reference in its entirety.

This application is related to U.S. patent application Ser. Nos. 13/219,505 and 13/219,497, both filed Aug. 26, 2011, the disclosures of each of which are incorporated herein by reference.

INTRODUCTION

The bones in the skull and face contain a series of air-filled cavities known as paranasal sinuses that are connected by passageways. The paranasal sinuses include frontal sinuses, sphenoid sinuses and maxillary sinuses. The paranasal sinuses are lined with mucus-producing epithelial tissue and are in communication with the nasal cavity. Normally, mucus produced by the epithelial tissue slowly drains out of each sinus through an opening known as an ostium. If the epithelial tissue of one of these passageways becomes inflamed for any reason, the cavities which drain through that passageway can become blocked. This blockage can be periodic (resulting in episodes of pain) or chronic. This interference with drainage of mucus (e.g., occlusion of a sinus ostium) can result in mucosal congestion within the paranasal sinuses. Chronic mucosal congestion of the sinuses can cause damage to the epithelium that lines the sinus with subsequent decreased oxygen tension and microbial growth (e.g., a sinus infection).

The term "sinusitis" refers generally to any inflammation or infection of the paranasal sinuses caused by bacteria, viruses, fungi (molds), allergies or combinations thereof. It has been estimated that chronic sinusitis (e.g., lasting more than 3 months) results in 18 million to 22 million physician office visits per year in the United States. Patients who suffer from sinusitis typically experience at least some of the following symptoms: headaches or facial pain, nasal congestion or post-nasal drainage, difficulty breathing through one or both nostrils, bad breath and/or pain in the upper teeth. Thus, one of the ways to treat sinusitis is by restoring the lost mucus flow.

SUMMARY

Medical devices which are adapted to be inserted into a patient for a limited period of time using minimally invasive insertion procedures for dilating a stenotic opening, such as a stenotic sinus opening, are provided. The devices and methods can be used for treating sinusitis and other nasal and/or sinus disorders.

In Situ Osmotic Anchor

In some embodiments, a device for dilating a stenotic opening of a maxillary sinus in a subject is provided. The device Includes: (a) a self-expanding osmotic driver configured to expand an expandable portion from a non-expanded configuration to an expanded configuration, the osmotic driver including a first osmotic driver and a second osmotic driver positioned distally to the first driver; and (b) the expandable portion disposed peripherally around the first and second osmotic drivers and configured to expand from the non-expanded configuration to the expanded configuration, where the non-expanded configuration is sized to be positioned within the stenotic opening. The second driver is configured to have (i) a faster rate of expansion than a rate of expansion of the first driver, and (ii) a duration of expansion less than a duration of expansion of the first driver, whereby the second driver is configured to prevent the device from being expelled from the stenotic opening and into the nasal cavity during device expansion.

Embodiments of the device may include that the second driver is configured to have a duration of expansion of 2 hours or less.

Embodiments of the device may include that the first and second drivers include an osmotically active agent, the second osmotic driver having a concentration of the agent greater than the concentration of the agent in the first driver.

Embodiments of the device may include that the osmotically active agent in the second driver has a concentration of 50 to 70 wt % and the osmotically active agent in the first driver has a concentration of 30 to 50 wt %.

Embodiments of the device may include that each of the first and second drivers includes an osmopolymer, the second driver having a concentration of the osmopolymer that is less than the concentration of the osmopolymer in the first driver.

Embodiments of the device may include that the osmopolymer in the first driver has a concentration of 30 to 70 wt % and the osmopolymer in the second driver has a concentration of 20 to 50 wt %.

Embodiments of the device may include that the second driver is configured to have a diameter greater than the diameter of the first driver during a period of stenotic opening dilation, and the second driver is configured to have a diameter less than the diameter of the first driver following said period of stenotic opening dilation.

Embodiments of the device may include that the period of stenotic opening dilation is 0.5 hours or more.

Embodiments of the device may include that the period of stenotic opening dilation is 2 hours or less.

Embodiments of the device may include that the device includes a conduit defining an interior lumen, where the conduit includes a distal end configured to be in fluid communication with an interior cavity of the maxillary sinus in the subject and a proximal end configured to be in fluid communication with a nasal cavity in the subject, and where the conduit is configured to allow fluid flow between the interior cavity of the maxillary sinus and the nasal cavity when the device is positioned within the stenotic opening.

Embodiments of the device may include that the expandable portion includes a semipermeable membrane.

Embodiments of the device may include that the device includes a proximal anchor proximate to the proximal end of the device, where the proximal anchor is configured to prevent the device from moving into a maxillary sinus cavity of the subject during device placement and expansion.

Wicking Agent

In some embodiments, a device for dilating a stenotic opening of a paranasal sinus in a subject is provided. The device includes a self-expanding osmotic driver, the self-expanding osmotic driver configured to expand an expandable portion from a non-expanded configuration to an expanded configuration, the expandable portion disposed peripherally around the driver and configured to expand from the non-expanded configuration to the expanded configuration, where the non-expanded configuration is sized to be positioned within the stenotic opening. The osmotic driver includes a wicking agent.

Embodiments of the device may include that the wicking agent includes hydroxypropyl cellulose.

Embodiments of the device may include that the wicking agent has an average particle size of 100 µm or less.

Embodiments of the device may include that the driver is configured to expand the expandable portion from the non-expanded configuration to the expanded configuration over a period of 0.5 hours or more.

Embodiments of the device may include that the driver is configured to expand the expandable portion from the non-expanded configuration to the expanded configuration over a period of 2 hours or less.

Embodiments of the device may include that the driver includes an osmotically active agent.

Embodiments of the device may include that the device includes a conduit defining an interior lumen, where the conduit includes a distal end configured to be in fluid communication with an interior cavity of the paranasal sinus in the subject and a proximal end configured to be in fluid communication with a nasal cavity in the subject, and where the conduit is configured to allow fluid flow between the interior cavity of the paranasal sinus and the nasal cavity when the device is positioned within the stenotic opening.

Embodiments of the device may include that the expandable portion includes a semipermeable membrane.

Embodiments of the device may include that the device includes a proximal anchor proximate to the proximal end of the device, where the proximal anchor is configured to maintain the device within the stenotic opening.

Insertion Device Circumferential Trigger

In some embodiments, a device for inserting a sinus dilator into a stenotic opening of a paranasal sinus of a patient is provided. The insertion device includes: a handheld member including (i) a handle sized to be grasped by a user's hand and having a grippable exterior surface; and (ii) a trigger activated by a user's thumb or finger; a hollow elongated member having a proximal end coupled to the handheld member and a distal end having an opening to an interior cavity of the hollow elongated member and a retention interface for removably coupling to a sinus dilator; and an interior elongated member extending within the interior cavity of the hollow elongated member and operatively connected to the trigger. The trigger extends around 25% or more of the exterior surface of the handle.

Embodiments of the insertion device may include that the trigger extends around 50% or more of the exterior surface of the handle.

Embodiments of the insertion device may include that the trigger extends around 75% or more of the exterior surface of the handle.

Embodiments of the insertion device may include that the trigger extends around the entire exterior surface of the handle.

Embodiments of the insertion device may include that the handle has a circular cross-section and the trigger extends around a percentage of a circumference of the handle.

Insertion Device with Low Profile Retention Tip

In some embodiments, a device for inserting a sinus dilator into a stenotic opening of a paranasal sinus of a patient is provided. The insertion device includes a handheld member including a handle and a trigger, a hollow elongated member having a proximal end coupled to the handheld member and a distal end coupled to a retention tip, and an interior elongated member coupled to the trigger and extending within an interior cavity of the hollow elongated member. The retention tip is angularly coupled to the distal end of the hollow elongated member with respect to the central passageway of the hollow elongated member. The retention tip also includes an opening to an interior cavity of the hollow elongated member.

Embodiments of the insertion device may include that a distal end of the interior elongated member is configured to extend through the opening in the retention tip into an interior cavity of the retention tip.

Embodiments of the insertion device may include that the interior elongated member is relatively displaceable with respect to the hollow elongated member such that upon actuation of the trigger, the interior elongated member is displaced proximally within the hollow elongated member. In certain embodiments, the interior elongated member is configured to decouple from the sinus dilator when the interior elongated member is displaced proximally within the hollow elongated member.

Embodiments of the insertion device may include that the interior elongated member is relatively displaceable with respect to the hollow elongated member such that upon actuation of the trigger, the interior elongated member is displaced distally within the hollow elongated member. In certain embodiments, the interior elongated member is configured to decouple the sinus dilator from the retention interface when the interior elongated member is displaced distally within the hollow elongated member.

Embodiments of the insertion device may include that the distal end of the hollow elongated member is substantially linear.

Embodiments of the insertion device may include that the retention tip is coupled to the distal end of the hollow elongated member at a position between the proximal and distal ends of the retention tip.

Embodiments of the insertion device may include that the retention tip has a length of 5 mm or less.

Humidity-Regulating Agent

In some embodiments, a packaged dilator for dilating a stenotic opening of a paranasal sinus in a subject is provided. The packaged dilator includes a device for dilating a stenotic opening of a paranasal sinus in a subject. The device includes: i) an expandable portion configured to expand from a non-expanded configuration to an expanded configuration, where the non-expanded configuration is sized to be positioned within the stenotic opening; and ii) a self-expanding osmotic driver configured to expand the expandable portion from the non-expanded configuration to the expanded configuration, where the expanded configuration dilates the stenotic opening. The packaged dilator also includes a sealed package containing the device, the sealed package being water impermeable and containing a humidity-regulating agent.

Embodiments of the packaged dilator may include that the osmotic driver includes a semipermeable membrane that includes a hydrophilic polymer having an equilibrium water content range, and the humidity-regulating agent maintains the water content of the hydrophilic polymer within the equilibrium water content range.

Embodiments of the packaged dilator may include that the osmotic driver includes an expandable osmotic core that expands upon exposure to water, and the humidity-regulating agent is configured to prevent the osmotic core from expanding while in the sealed package.

Embodiments of the packaged dilator may include that the humidity-regulating agent is configured to maintain the relative humidity within the sealed package at a relative humidity of from 30% to 60%.

Embodiments of the packaged dilator may include that the driver is configured to expand the expandable portion from the non-expanded configuration to the expanded configuration over a period of 0.5 hours or more.

Embodiments of the packaged dilator may include that the driver is configured to expand the expandable portion from the non-expanded configuration to the expanded configuration over a period of 2 hours or less.

Embodiments of the packaged dilator may include that the driver includes an osmotically active agent.

Embodiments of the packaged dilator may include that the device includes a conduit defining an interior lumen, where the conduit includes a distal end configured to be in fluid communication with an interior lumen of the paranasal sinus in the subject and a proximal end configured to be in fluid communication with a nasal cavity in the subject, and where the conduit is configured to allow fluid flow between the interior lumen of the paranasal sinus and the nasal cavity when the device is positioned within the stenotic opening.

Embodiments of the packaged dilator may include that the expandable portion includes a semipermeable membrane.

Embodiments of the packaged dilator may include that the device includes a proximal anchor proximate to the proximal end of the device, where the proximal anchor is configured to maintain the device within the stenotic opening.

Sinus Dilator Proximal Anchor

In some embodiments, a device for dilating a stenotic opening of a maxillary sinus in a subject is provided. The device includes: (a) a self-expanding driver configured to expand an expandable portion from a non-expanded configuration to an expanded configuration; and (b) the expandable portion disposed peripherally around the driver and configured to expand from the non-expanded configuration to the expanded configuration, where the non-expanded configuration is sized to be positioned within the stenotic opening; and (c) a proximal anchor proximate to the proximal end of the device, the proximal anchor being sized and configured to prevent the device from passing through the stenotic opening into the maxillary sinus cavity. The device has an elongated proximal end having a sufficient length to contact a wall of the nasal cavity facing the stenotic opening when the device is positioned within the stenotic opening. Embodiments of the device may include that the device has a length, measured from a point on the device that is immediately adjacent to the nasal passageway side of the sinus opening, to the proximal end of the device, of 3 to 6 mm.

Embodiments of the device may include that the elongated proximal end forms at least a portion of the proximal anchor.

Embodiments of the device may include that the elongated proximal end is configured to prevent the device from being squeezed out of the sinus opening and into the nasal passageway during device expansion.

Embodiments of the device may include that the proximal anchor includes a member extending radially outward from an axis of the device.

Embodiments of the device may include that the proximal anchor includes a pair of said radially outward extending members.

Embodiments of the device may include that the members are positioned on opposite sides of a longitudinal axis of the device.

Embodiments of the device may include that each of the members extends radially outward from the axis of the device a distance of 3 mm or more.

Embodiments of the device may include that each of the members extends radially outward from the axis of the device a distance of 4 to 8 mm.

Embodiments of the device may include that the driver is configured to expand the expandable portion to a diameter of 7 mm or less.

Embodiments of the device may include that the driver is configured to expand the expandable portion from the non-expanded configuration to the expanded configuration over a period of 0.5 hours or more.

Embodiments of the device may include that the driver is configured to expand the expandable portion from the non-expanded configuration to the expanded configuration over a period of 2 hours or less.

Embodiments of the device may include that the driver is configured to expand the expandable portion by at least one of osmosis, a shape memory metal, a spring, a swellable polymer, a thermal expansion of a gas, a thermal expansion of a liquid, a gas-generating chemical reaction, and a phase change expansion of a material.

Embodiments of the device may include that the driver includes an osmotically active agent.

Embodiments of the device may include that the expandable portion includes a semipermeable membrane.

Embodiments of the device may include that the device includes a conduit defining an interior lumen, where the conduit includes a distal end configured to be in fluid communication with an interior lumen of the maxillary sinus in the subject and a proximal end configured to be in fluid communication with a nasal cavity in the subject, and where the conduit is configured to allow fluid flow between the maxillary sinus cavity and the nasal cavity when the device is positioned within the stenotic opening.

Sinus Dilator Cone-Shaped Distal Tip

In some embodiments, a device for dilating a stenotic opening of a paranasal sinus in a subject is provided. The device includes: (a) a self-expanding driver configured to expand an expandable portion from a non-expanded configuration to an expanded configuration, the expandable portion disposed peripherally around the driver and configured to expand from the non-expanded configuration to the expanded configuration, where the non-expanded configuration is sized to be positioned within the stenotic opening; and (b) a tip disposed on a distal end of the device, the tip being cone-shaped.

Embodiments of the device may include that the tip is comprised of a material such as metal, plastic, or ceramic.

Embodiments of the device may include that the tip has an apex angle of 20° to 70°.

Embodiments of the device may include that the tip has an apex angle of 50° to 70°.

Embodiments of the device may include that the tip has an apex angle of 60°.

Embodiments of the device may include that the tip includes a proximal surface in contact with the driver and configured to direct expansion of the driver radially outwardly from an axis of the device.

Embodiments of the device may include that the device has a passageway extending through at least a distal end of the device and the tip includes a proximally extending post that engages the passageway.

Embodiments of the device may include that the device includes a conduit defining an interior lumen, where the conduit includes a distal end configured to be in fluid communication with an interior lumen of the paranasal sinus in the subject and a proximal end configured to be in fluid communication with a nasal cavity in the subject, and where the conduit is configured to allow fluid flow between the interior lumen of the paranasal sinus and the nasal cavity when the device is positioned within the stenotic opening.

Embodiments of the device may include that the driver is configured to expand the expandable portion from the non-expanded configuration to the expanded configuration over a period of 0.5 hours or more.

Embodiments of the device may include that the driver is configured to expand the expandable portion from the non-expanded configuration to the expanded configuration over a period of 2 hours or less.

Embodiments of the device may include that the driver is configured to expand the expandable portion by at least one of osmosis, a shape memory metal, a spring, a swellable polymer, a thermal expansion of a gas, a thermal expansion of a liquid, a gas-generating chemical reaction and a phase change expansion of a material.

Embodiments of the device may include that the driver includes an osmotically active agent.

Embodiments of the device may include that the expandable portion includes a semipermeable membrane.

Embodiments of the device may include that the device includes a proximal anchor proximate to the proximal end of the device, where the proximal anchor is configured to maintain the device within the stenotic opening.

Sinus Dilator with a Drug Reservoir

In some embodiments, a device for dilating a stenotic opening of a paranasal sinus in a subject is provided. The device includes: (a) a self-expanding osmotic driver including a first osmotic driver and a second osmotic driver positioned distal to the first driver, the self-expanding osmotic driver configured to expand an expandable portion from a non-expanded configuration to an expanded configuration, the expandable portion disposed peripherally around the first and second osmotic drivers and configured to expand from the non-expanded configuration to the expanded configuration, where the non-expanded configuration is sized to be positioned within the stenotic opening; and (b) a drug reservoir positioned between the first and second drivers and within the periphery of the expandable portion.

Embodiments of the device may include that the drug reservoir is configured to release a drug as the first and second osmotic drivers expand from a non-expanded configuration to an expanded configuration.

Embodiments of the device may include that the expandable portion includes an elastic semipermeable membrane, where the drug diffuses through the membrane during use of the device.

Embodiments of the device may include that the drug is water soluble.

Embodiments of the device may include that the drug is an antibiotic, an anti-inflammatory drug, a local anesthetic, an analgesic, or a combination thereof.

Embodiments of the device may include that the driver is configured to expand the expandable portion from the non-expanded configuration to the expanded configuration over a period of 0.5 hours or more.

Embodiments of the device may include that the driver is configured to expand the expandable portion from the non-expanded configuration to the expanded configuration over a period of 2 hours or less.

Embodiments of the device may include that each of the first and second osmotic drivers includes an osmotically active agent.

Embodiments of the device may include that the device includes a conduit defining an interior lumen, where the conduit includes a distal end configured to be in fluid communication with an interior cavity of the paranasal sinus in the subject and a proximal end configured to be in fluid communication with a nasal cavity in the subject, and where the conduit is configured to allow fluid flow between the interior cavity of the paranasal sinus and the nasal cavity when the device is positioned within the stenotic opening.

Embodiments of the device may include that the expandable portion includes a semipermeable membrane.

Embodiments of the device may include that the device includes a proximal anchor proximate to the proximal end of the device, where the proximal anchor is configured to maintain the device within the stenotic opening during device expansion.

Sinus Dilator with a Drug in the Osmotic Driver

In some embodiments, a device for dilating a stenotic opening of a paranasal sinus in a subject is provided. The device includes a self-expanding osmotic driver including an osmotically active agent, the self-expanding osmotic driver configured to expand an expandable portion from a non-expanded configuration to an expanded configuration, the expandable portion disposed peripherally around the driver and configured to expand from the non-expanded configuration to the expanded configuration, where the non-expanded configuration is sized to be positioned within the stenotic opening. The osmotically active agent includes a drug.

Embodiments of the device may include that the expandable portion includes an elastic semipermeable membrane, where the drug diffuses through the membrane during use of the device.

Embodiments of the device may include that the drug is water soluble.

Embodiments of the device may include that the drug is an antibiotic, an anti-inflammatory drug, a local anesthetic, an analgesic, or a combination thereof.

Embodiments of the device may include that the driver is configured to expand the expandable portion from the non-expanded configuration to the expanded configuration over a period of 0.5 hours or more.

Embodiments of the device may include that the driver is configured to expand the expandable portion from the non-expanded configuration to the expanded configuration over a period of 2 hours or less.

Embodiments of the device may include that each of the first and second osmotic drivers includes an osmotically active agent.

Embodiments of the device may include that the device includes a conduit defining an interior lumen, where the conduit includes a distal end configured to be in fluid communication with an interior cavity of the paranasal sinus in the subject and a proximal end configured to be in fluid communication with a nasal cavity in the subject, and where the conduit is configured to allow fluid flow between the interior cavity of the paranasal sinus and the nasal cavity when the device is positioned within the stenotic opening.

Embodiments of the device may include that the device includes a proximal anchor proximate to the proximal end of the device, where the proximal anchor is configured to maintain the device within the stenotic opening during device expansion.

Tablet Compression Force

In some embodiments, a method of making a device for dilating a stenotic opening of a paranasal sinus in a subject is provided. The method includes forming an osmotic driver in the form of a tablet comprised of an osmotically active agent, an osmopolymer and an expandable membrane disposed peripherally therearound, the driver being configured to expand from a non-expanded configuration to an expanded configuration, where the non-expanded configuration is sized to be positioned within the stenotic opening. The forming includes compressing the tablet such that the tablet is formed having a smooth outer surface with no flashing.

Embodiments of the method may include that the forming includes compressing the osmotically active agent and the osmopolymer in a tablet press.

Embodiments of the method may include that the compressing includes compressing the tablet using a compression force of 100 lbs or less.

Embodiments of the method may include that the compressing includes compressing the tablet using a compression force of 20 to 70 lbs.

Embodiments of the method may include that the compressing includes compressing the tablet using a compression pressure of 15 to 65 mPa.

Embodiments of the method may include that the compressing includes compressing the tablet using a compression pressure of 30 to 65 mPa.

Embodiments of the method may include that the osmotically active agent is a salt.

Embodiments of the method may include that the osmopolymer is a hydrogel-forming osmopolymer.

Embodiments of the method may include that the expandable membrane is an elastic semipermeable membrane.

Insertion Device Recessed Push Rod

In some embodiments, a device for inserting a sinus dilator into a stenotic opening of a paranasal sinus of a patient is provided. The insertion device includes a handheld member including a handle and a trigger, a hollow elongated member having a proximal end coupled to the handheld member and a distal end having an opening to an interior cavity of the hollow elongated member, and an interior elongated member extending within the interior cavity of the hollow elongated member. The hollow elongated member includes a retention interface configured to removably couple to a proximal end of a sinus dilator, and where a distal end of the interior elongated member is recessed from the distal end of the hollow elongated member a distance sufficient to accommodate insertion of the proximal end of the sinus dilator.

Embodiments of the insertion device may include that the interior elongated member is relatively displaceable with respect to the hollow elongated member such that upon actuation of the trigger, the interior elongated member is displaced distally within the hollow elongated member.

Embodiments of the insertion device may include that the trigger is slidably coupled to the handle and the trigger is coupled to the interior elongated member such that sliding the trigger relative to the handle displaces the interior elongated member distally relative to the hollow elongated member.

Embodiments of the insertion device may include that the proximal end of the sinus dilator includes an elongated proximal anchor.

Insertion Device Distal Tip Angle

In some embodiments, a device for inserting a sinus dilator into a stenotic opening of a maxillary sinus of a patient is provided. The insertion device includes: a handheld member including a handle and a trigger; a hollow elongated member having a proximal end coupled to the handheld member and a distal end having a retention interface for removably coupling to the sinus dilator and a middle section extending between the distal and proximal ends, the middle section having an axis; an interior elongated member extending within the interior cavity of the hollow elongated member. The distal end of the hollow elongated member is oriented at an angle of 105° to 115° relative to the axis.

Embodiments of the insertion device may include that the angle is 110°.

Figure 1:
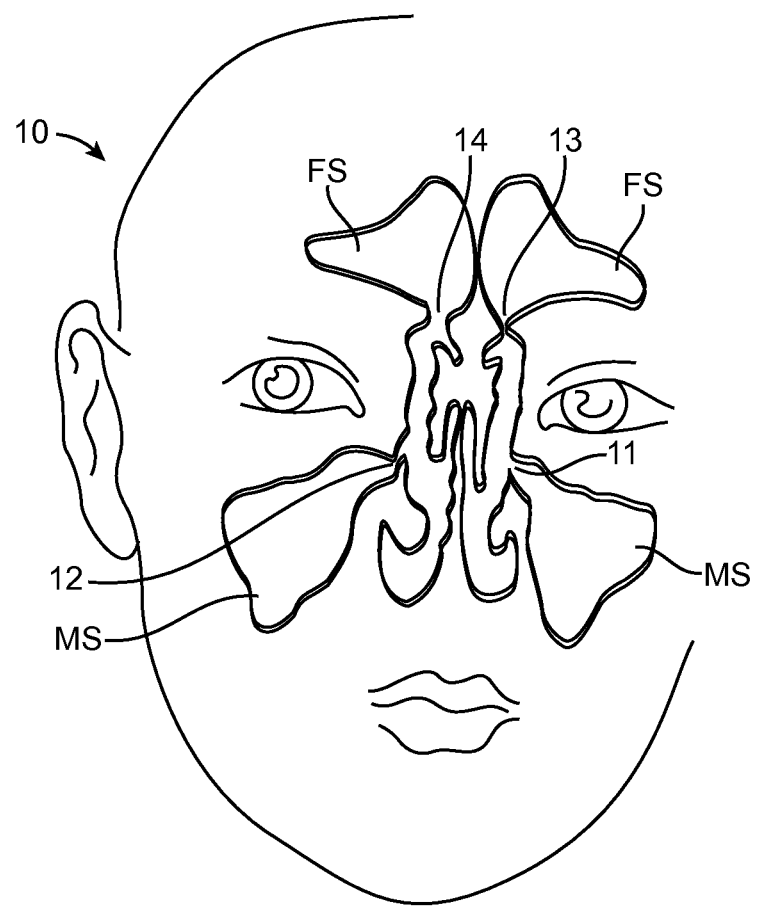
FIG. 1 is a partial cutaway view of a human head showing the positions of the frontal sinuses (FS) and the maxillary sinuses (MS)

Before embodiments of the present disclosure are described in greater detail, it is to be understood that these embodiments are not limited to the particular aspects described, and as such may, of course, vary. It is also to be understood that the terminology used herein is for the purpose of describing particular embodiments only, and is not intended to be limiting, since the scope of the embodiments is embodied by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within embodiments of the present disclosure. The upper and lower limits of these smaller ranges may independently be included in the smaller ranges and are also encompassed within the embodiments, subject to any specifically excluded limit in the stated range. Where the stated range includes one or both of the limits, ranges excluding either or both of those included limits are also included in the embodiments.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present embodiments, representative illustrative methods and materials are now described.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, it will be readily apparent to one of ordinary skill in the art in light of the teachings herein that certain changes and modifications may be made thereto without departing from the spirit and scope of the appended claims. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. To the extent such publications may set out definitions of a term that conflict with the explicit or implicit definition of the present disclosure, the definition of the present disclosure controls. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

DETAILED DESCRIPTION

Medical devices which are adapted to be inserted into a patient for a limited period of time using minimally invasive insertion procedures for dilating a stenotic opening, such as a stenotic sinus opening, are provided. The devices and methods can be used for treating sinusitis and other nasal and/or sinus disorders.

Devices and Methods for Dilating a Stenotic Opening of a Paranasal Sinus in a Subject Aspects of the present disclosure include devices and methods for dilating a stenotic opening of a paranasal sinus in a subject. The device (e.g., sinus dilator) includes an expandable portion configured to expand from a non-expanded configuration to an expanded configuration, where the non-expanded configuration is sized to be positioned within the stenotic opening, and a driver configured to expand the expandable portion from the non-expanded configuration to the expanded configuration, where the expanded configuration dilates the stenotic opening.

The term "stenotic opening" refers to an abnormal narrowing of a biological passageway, such as a paranasal sinus opening. In certain embodiments, the device includes an osmotic driver configured to expand an expandable portion from a non-expanded configuration to an expanded configuration, and the expandable portion disposed peripherally around the driver and configured to expand from the non-expanded configuration to the expanded configuration, where the non-expanded configuration is sized to be positioned within the stenotic opening.

In certain embodiments, the driver is self-expanding when in contact with tissue of the subject. By "self-expanding" is meant that the driver may expand from the non-expanded configuration to the expanded configuration without external intervention from a user or a health care practitioner. For example, the self-expanding driver may be self-contained, such that the driver is configured to expand without connection to an external pressure source. As such, self-expanding drivers as described herein function without the need for an external pressure source or a pressure monitoring device (e.g., as with a balloon catheter). In some cases, the self-expanding driver expands from the non-expanded configuration to the expanded configuration upon absorbing fluid from the surrounding environment when the device is in use. For instance, the self-expanding driver may expand from the non-expanded configuration to the expanded configuration upon absorbing water from the surrounding tissues of the stenotic opening when the device is in use. Self-expanding drivers may be configured to expand the expandable portion of the device by various ways, such as, but not limited to, an osmotic agent, a swellable agent (e.g., a swellable polymer), combinations thereof, and the like. In some instances, the driver is configured to expand the expandable portion by at least one of osmosis, a shape memory metal, a spring, a swellable polymer, a thermal expansion of a gas, a thermal expansion of a liquid, a gas-generating chemical reaction and a phase change expansion of a material.

In certain embodiments, the driver includes an osmotic agent. As used herein, the terms "osmotic agent," "osmotically active agent" and "osmoagent" are used interchangeably and refer to an agent that facilitates the imbibition of water from a region of high water potential (e.g., low solute concentration) through a semipermeable membrane to a region of low water potential (e.g., high solute concentration) until a state of dynamic equilibrium is reached. In some instances, the osmotically active agent may be configured to absorb water flowing through a semipermeable membrane from the surrounding tissues after insertion of the device into the stenotic opening of the subject and expand. In certain embodiments, the osmotic agent is configured to have a zero order rate of expansion. By "zero order" is meant that the rate of volume expansion of the osmotic agent is approximately constant over time and is independent of the surrounding solute concentration.

In certain embodiments, the driver is configured to begin expanding upon insertion of the device into the stenotic opening of the subject. The terms "insert" or "insertion" are used herein interchangeably to describe the positioning of a device in a stenotic opening of a subject for a period of time. In some instances, the driver is configured to begin expanding within seconds or minutes after insertion of the device into the stenotic opening. In some cases, the driver is configured to begin expanding in 60 min or less, such as 45 min or less, or 30 min or less, including 10 min or less, or 5 min or less, such as 1 min or less, after insertion of the device into the stenotic opening. In some instances, the driver is configured to continue to expand for a certain period of time after the device has been inserted into the stenotic opening of the subject. For example, the driver may be configured to continue to expand for 30 min or more, such as 45 min or more, including 60 min or more, or 90 min or more, 120 min or more, or 180 min or more, or 240 min or more, or 300 min or more after the device has been inserted into the stenotic opening of the subject.

In certain embodiments, the driver takes a certain amount of time to expand the expandable portion from the non-expanded configuration to the expanded configuration. For instance, in some cases the driver is configured to expand the expandable portion from the non-expanded configuration to the expanded configuration over a period of 0.5 hours or more, such as 1 hour or more, or 2 hours or more, or 4 hours or more, or 6 hours or more, or 8 hours or more, or 10 hours or more, or 12 hours or more, or 24 hours or more, or 48 hours or more, or 72 hours or more, etc. In some instances, the driver is configured to expand the expandable portion from the non-expanded configuration to the expanded configuration over a period of 24 hours or less, such as 12 hours or less, or 10 hours or less, or 8 hours or less, or 6 hours or less, or 4 hours or less, or 2 hours or less, 1.5 hours or less, or 1 hours or less, or 0.5 hours or less. As such, in certain instances, the driver is configured to expand the expandable portion from the non-expanded configuration to the expanded configuration over a period ranging from 0.5 hours to 24 hours, such as 0.5 hour to 12 hours, including 0.5 hour to 10 hours, or 1 hour to 8 hours, or 1 hour to 6 hours, or 1 hour to 4 hours, or 1 hour to 2 hours.

In certain embodiments, the driver is configured to expand the expandable portion to a diameter of 10 mm or less, such as 9 mm or less, or 8 mm or less, or 7 mm or less, or 6 mm or less, or 5 mm or less, or 4 mm or less, or 3 mm or less, or 2 mm or less, or 1 mm or less. In some cases, the driver is configured to expand the expandable portion to a diameter of 7 mm or less.

As used herein, the term "distal" refers to the end of a device (e.g., a sinus dilator device or insertion device), or a component thereof, that is positioned towards the end of the device that is inserted through or closest to a paranasal sinus opening of the subject. For example, the distal end of a sinus dilator device is the end of the device that is inserted through the paranasal sinus opening of the subject and remains within the sinus cavity during use. A device (e.g., a sinus dilator device or insertion device), or a component thereof, may also include a proximal end. As used herein, the term "proximal" refers to the end of the device, or component thereof, that is positioned towards the end of the device that remains on the nasal cavity side of the stenotic opening or remain external to the subject during use. For example, the proximal end of a sinus dilator device is the end of the device that remains on the nasal cavity side of the stenotic opening when the sinus dilator device is positioned in the stenotic opening during use.

Embodiments of the presently disclosed devices include an expandable portion. The expandable portion is configured to expand from a non-expanded configuration to an expanded configuration. In certain embodiments, the expandable portion is configured to expand in size from a non-expanded configuration to an expanded configuration. The expandable portion may be configured to expand in size without significantly increasing in volume, such as by stretching in one or more dimensions from the non-expanded configuration. The expandable portion may be positioned peripherally around the driver. For instance, the expandable portion may be disposed on an exterior surface of the driver. In these embodiments, expansion of the underlying driver expands the expandable portion from its non-expanded configuration to its expanded configuration.

Aspects of the present disclosure include devices that have an expandable portion, where the expandable portion includes a membrane. The membrane may be an elastic membrane, such that the membrane is configured to expand from the non-expanded configuration to the expanded configuration, as described herein. In certain instances, the membrane is a semipermeable membrane. By "semipermeable" is meant a membrane that is permeable to solvent but not significantly permeable to solute across a concentration gradient, such as a membrane that allows solvent (e.g., water) molecules to pass through the membrane by osmosis from a region of low solute concentration to a region of high solute concentration until a state of dynamic equilibrium is reached. For instance, a semipermeable membrane may be configured to allow water to pass through the membrane by osmosis from a region of low solute concentration (e.g., high water potential) to a region of high solute concentration (e.g., low water potential) until a state of dynamic equilibrium is reached.

In certain embodiments, the expandable portion includes a membrane, where the membrane is an impermeable membrane. By "impermeable" is meant a membrane that is not significantly permeable to solvent or solute. Impermeable membranes do not allow significant amounts of solvent (e.g., water) or solute molecules to pass through the membrane by osmosis even in the presence of a solute concentration gradient across the membrane.

In certain embodiments, the device includes a conduit that defines an interior lumen of the device. The conduit includes a distal end configured to be in fluid communication with an interior lumen of the paranasal sinus in the subject. In some cases, the conduit may be configured to allow fluid flow between the paranasal sinus in the subject and the nasal cavity when the device is positioned within the stenotic opening. In some instances, the conduit is configured to allow fluid and/or air to flow from the paranasal sinus to the nasal cavity of the subject. For example, the conduit may be configured to facilitate drainage of fluid from the paranasal sinus in the subject to the nasal cavity when the device is positioned within the stenotic opening. In some cases, the conduit may be configured to facilitate the flow of air into and out of the paranasal sinus in the subject.

In certain embodiments, the driver is disposed on an exterior surface of the conduit. The driver may be disposed on the exterior surface of the conduit at a position between the distal end and the proximal end of the conduit. For example, the driver may be positioned between a distal anchor at the distal end of the conduit and a proximal anchor at the proximal end of the conduit. As described herein, the expandable portion may be positioned peripherally around the driver. Thus, in these embodiments, the driver is disposed between the exterior surface of the conduit and the overlying expandable portion. Expansion of the driver expands the overlying expandable portion from its non-expanded configuration to its expanded configuration.

Aspects of the driver further include embodiments where the driver completely surrounds the conduit. The driver may be disposed on the exterior surface of the conduit around the entire periphery of the conduit. In certain embodiments, the driver surrounds the conduit around the central portion of the conduit, where the distal end of the conduit may have a distal anchor and the proximal end of the conduit may have a proximal anchor, as described in more detail herein. In some instances, the driver includes one or more subunits, where each subunit is disposed on the exterior surface of the conduit. The one or more driver subunits may be positioned such that they are in contact with the adjacent one or more driver subunits. Alternatively, the one or more driver subunits may be positioned such that there is a channel between the driver subunits. In certain instances, the channel between the driver subunits extends along the exterior surface of the conduit from the distal end of the conduit to the proximal end of the conduit. The channels may be configured to allow fluid and/or air to flow between the paranasal sinus and the nasal cavity of the subject. In certain cases, the channels are configured to allow fluid and/or air to flow from the paranasal sinus to the nasal cavity of the subject. For example, the channels may be configured to facilitate drainage of fluid from the paranasal sinus in the subject to the nasal cavity when the device is positioned within the stenotic opening. In some cases, the channels may be configured to facilitate the flow of air into and out of the paranasal sinus in the subject.

In certain embodiments, the walls of the conduit are substantially rigid. The walls of the conduit may be substantially rigid, such that the conduit maintains substantially the same shape and size during use of the device. For instance, the conduit may maintain substantially the same interior diameter during use of the device. In some instances, the walls of the conduit are substantially rigid, such that pressure exerted on the exterior surface of the conduit by the driver does not significantly decrease the interior diameter of the conduit. For example, the walls of the conduit may be substantially rigid, such that the conduit is not crushed by the driver during use of the device. In some instances, the driver is configured to expand radially outward from the conduit. As discussed above, the walls of the conduit may be substantially rigid, thus expansion of the driver may be directed radially outward away from the substantially rigid walls of the conduit. Expansion of the driver radially outward from the conduit may facilitate dilation of the stenotic opening.

In certain embodiments, the walls of the conduit are substantially non-collapsible. The walls of the conduit may be substantially non-collapsible, such that the conduit is configured to maintain an opening in the conduit during use of the device. For example, the walls of the conduit may be substantially non-collapsible, such that the conduit is not crushed by the driver during use of the device. In some cases, a non-collapsible conduit maintains substantially the same shape and size during use of the device. For instance, the conduit may maintain substantially the same interior diameter during use of the device. In some instances, the walls of the conduit are substantially non-collapsible, such that pressure exerted on the exterior surface of the conduit by the driver does not significantly decrease the interior diameter of the conduit. As discussed above, the driver may be configured to expand radially outward from the conduit and, as such, the walls of the conduit may be substantially non-collapsible, such that expansion of the driver is directed radially outward away from the substantially non-collapsible walls of the conduit. Expansion of the driver radially outward from the conduit may facilitate dilation of the stenotic opening. A substantially non-collapsible conduit may be rigid, as described above, or may be flexible and adapted to bend from its original shape. In some instances, a flexible conduit facilitates insertion of the sinus dilator in a sinus ostium.

In certain instances, the conduit includes a membrane. The conduit membrane may be a semipermeable membrane. In certain instances, the conduit membrane is a non-collapsible semipermeable membrane. In some cases, the conduit membrane is a rigid semipermeable membrane. The membrane may be configured to be permeable to solvent but not significantly permeable to solute across a concentration gradient, such that the membrane allows solvent (e.g., water) molecules to pass through the membrane by osmosis from a region of low solute concentration to a region of high solute concentration until a state of dynamic equilibrium is reached. For instance, the membrane may be configured to allow water to pass through the membrane by osmosis from an interior lumen of the conduit to the surrounding driver until a state of dynamic equilibrium is reached.

In some embodiments, the device includes a conduit that includes a semipermeable membrane, a surrounding driver, and an overlying expandable portion that includes a semipermeable membrane. In these embodiments, the device may be configured to allow solvent (e.g., water) to pass through both the semipermeable expandable portion membrane by osmosis and through the semipermeable conduit membrane by osmosis. For example, the device may be configured to allow solvent to pass through the semipermeable expandable membrane from the surrounding tissues to the underlying driver, and also allow solvent to pass through the semipermeable conduit membrane from an interior lumen of the conduit to the surrounding driver.

In other embodiments, the device includes a conduit that includes a semipermeable membrane, a surrounding driver, and an overlying expandable portion that includes an impermeable membrane. In these embodiments, the device may be configured to allow solvent (e.g., water) to pass through the semipermeable conduit membrane by osmosis but not allow significant amounts of solvent (e.g., water) to pass through the impermeable expandable portion membrane. For example, the device may be configured to allow solvent to pass through the semipermeable conduit membrane from an interior lumen of the conduit to the surrounding driver, but not allow significant amount of solvent to pass through the impermeable expandable portion membrane to the driver.

In yet other embodiments, the conduit includes an impermeable material. In some cases, the impermeable material is an impermeable membrane. For instance, the device may include a conduit that includes an impermeable membrane, a surrounding driver, and an overlying expandable portion that includes a semipermeable membrane. In these embodiments, the device may be configured to allow solvent (e.g., water) to pass through the semipermeable expandable membrane by osmosis but not allow significant amounts of solvent (e.g., water) to pass through the impermeable conduit membrane. For example, the device may be configured to allow solvent to pass through the semipermeable expandable portion membrane from the surrounding tissues to the underlying driver, but not allow significant amount of solvent to pass through the impermeable conduit membrane from the interior lumen of the conduit to the surrounding driver.

Aspects of the device may include a distal anchor configured to maintain the device within the stenotic opening during use of the device. The distal anchor may be connected to the device proximate to the distal end of the device. For example, the distal anchor may be connected to the device proximate to the distal end of the conduit. In some cases, the distal anchor is configured to prevent the device from premature explantation from the stenotic opening. The distal anchor may facilitate maintaining the device within the stenotic opening for a desired period of time until the device is removed from the stenotic opening by the user or a health care professional. In certain embodiments, the distal anchor is a mechanical anchor, such as, but not limited to, a hook, a barb, a clamp, a tether and the like. In certain cases, the distal anchor is configured to maintain the device within the stenotic opening by having a diameter that is greater than the diameter of the stenotic opening.

In some instances, the device has a frictional surface on an exterior surface of the device. The frictional surface may be configured to increase the friction between the exterior surface of the device and the surrounding tissues when the device is in use. Increasing the friction between the exterior surface of the device and the surrounding tissues may facilitate retention of the device in the stenotic opening of the subject during use. For example, the frictional surface may have a rough topography that includes an exterior surface shaped as, for example, washboard, rings, waffle pattern, snow tire pattern, pebble finish, shark skin texture, combinations thereof, and the like.

In certain cases, the device includes an adhesive disposed on an exterior surface of the device. In some cases, the membrane includes an adhesive. The membrane may be configured such that the adhesive elutes to the external surface of the device during use. The adhesive may facilitate retention of the device in the stenotic opening of the patient during use. Examples of suitable adhesives include, but are not limited to, carbomer, low molecular weight hydroxypropyl methylcellulose, polyvinyl pyrrolidone, combinations thereof, and the like.

In some cases, the distal anchor is configured to allow the device to be inserted into the stenotic opening. The distal anchor may have an outside diameter that is substantially the same as the outside diameter of the device when the device is in a non-expanded configuration. In some instances, the distal anchor has an outside diameter that is greater than the diameter of the conduit. In certain embodiments, the distal anchor has a tapered shape, such that the distal end of the distal anchor has a diameter that is less than the diameter of the proximal end of the distal anchor (see e.g., FIGS. 5 and 6). In certain embodiments, the distal anchor is configured such that the distal anchor has a diameter that is smaller during insertion of the device into the stenotic opening as compared to the diameter of the distal anchor after the anchor portion of the device has been inserted into the paranasal sinus.

In certain embodiments, the distal anchor is a flexible anchor. In some cases, the flexible distal anchor is configured to have a configuration that has a smaller diameter during insertion of the device into the stenotic opening as compared to the diameter of the flexible distal anchor after the anchor portion of the device has been inserted into the paranasal sinus. For instance, the flexible distal anchor may be configured to fold into a configuration that has a smaller diameter during insertion of the device into the stenotic opening as compared to the diameter of the flexible distal anchor after the anchor portion of the device has been inserted into the paranasal sinus. The distal anchor may include one or more subunits that are connected to and extend radially outward from the conduit. The subunits of the distal anchor may be flexible, such that during insertion of the device into the stenotic opening, the subunits fold into a configuration where the distal anchor has an outside diameter that is less than the diameter of the distal anchor when the subunits are fully extended. Once the distal end of the device has been inserted into the paranasal sinus, the subunits may be free to unfold back to their extended configuration, thus anchoring the device within the stenotic opening.

Aspects of the device may include a proximal anchor configured to maintain the device within the stenotic opening during use of the device (see e.g., FIGS. 3-7). The proximal anchor may be connected to the device proximate to the proximal end of the device. For example, the proximal anchor may be connected to the device proximate to the proximal end of the conduit. In some cases, the proximal anchor is configured to prevent the device from being inserted too far or completely into the paranasal sinus of the subject. The proximal anchor may facilitate maintaining the device within the stenotic opening for a desired period of time until the device is removed from the stenotic opening by the user or a health care professional. In some cases, the proximal anchor has an outside diameter that is greater than the diameter of the conduit. For instance, the proximal anchor may have an outside diameter that is greater than the diameter of the device when the device is in a non-expanded configuration.

In some embodiments, the device includes an attachment portion configured to facilitate removal of the device from the stenotic opening. The attachment portion may be configured to allow a removal device to be attached to the device. For example, the attachment portion of the device may include a structure, such as, but not limited to, a loop, a tether or a hook. The removal device may include a corresponding structure that allows for attachment of the removal device to the attachment portion of the device. In some instances, the device includes a loop and the removal device includes a hook. In other embodiments, the device includes a hook and the removal device includes a loop. In either embodiment, insertion of the hook into the loop connects the device to the removal device and may facilitate removal of the device from the stenotic opening.

In some cases, the attachment portion may protrude from the device to facilitate connection of the removal device to the attachment portion of the device. The attachment portion may be disposed at or near the proximal end of the device to facilitate removal of the device from the stenotic opening. For example, the attachment portion may be disposed on the proximal anchor at the proximal end of the device. In certain cases, the attachment portion may be connected to the conduit proximate to the proximal end of the device.

Additional aspects of the devices and methods for dilating a stenotic opening of a paranasal sinus in a subject are described in more detail in U.S. patent application Ser. Nos. 13/219,505 and 13/219,497, both filed Aug. 26, 2011, the disclosures of each of which are incorporated herein by reference.

Devices and Methods for Inserting a Sinus Dilator

Aspects of the present disclosure include an insertion device adapted to insert a sinus dilator into a stenotic opening of a paranasal sinus in a subject patient using minimally invasive insertion procedures. The insertion device and methods can be used to treat sinusitis and other nasal and/or sinus disorders.

The insertion device includes a handheld member coupled to a hollow elongated member. By "hollow" is meant that the hollow elongated member includes a central passageway that extends through the length of the hollow elongated member. For example, the hollow elongated member may be a tube or a cannula. In certain embodiments, the proximal end of the hollow elongated member may be coupled to a handheld member and the distal end of the hollow elongated member is dimensioned to pass through a nasal cavity of a subject. A sinus dilator, as described above, may be coupled to the distal end of an insertion device, which may then be inserted into the nasal cavity of a subject. The sinus dilator is then positioned within a stenotic sinus opening, which may be partially or completely occluded.

In certain embodiments, the insertion device also includes an interior elongated member positioned within the hollow elongated member and extending at least a portion of the length of the hollow elongated member. The interior elongated member has a proximal end coupled to the handheld member and dimensioned to fit within the hollow elongated member. The distal end of the interior elongated member may include a retention interface that removably couples to a sinus dilator. The sinus dilator may be coupled to the retention interface (e.g., slid on, snapped on, clamped on, etc.) and then the distal end of the insertion device may be inserted within the nasal cavity to position the sinus dilator within the stenotic opening. In certain embodiments, the retention interface and sinus dilator are configured to be removably coupled, thus the sinus dilator may be decoupled from the insertion device and left within the stenotic opening.

The retention interface may include various coupling mechanisms to retain the sinus dilator coupled to the insertion device. In some instances, the retention interface is sized and shaped to fit within a sinus dilator, e.g., within the central passageway of the sinus dilator, or a passageway, recess, slot, etc. within the sinus dilator. The retention interface may provide sufficient retention to maintain the sinus dilator coupled while permitting some light axial and off-axis loads or bending moments. In some instances, the sinus dilator is sufficiently rigidly affixed to the retention interface to enable a user (e.g., physician) to push the sinus dilator through a stenotic opening even when the opening is completely shut.

As summarized above, the insertion device also includes a handheld member. As the handheld member is held by the user, it is configured to have a shape and size that is amenable to gripping by the user's hand. The insertion device may include, for example, a trigger that is located in a position for the user to actuate the trigger in order to decouple a sinus dilator coupled to the distal end of the insertion device. For instance, the insertion device may be shaped and sized to be gripped by a physician's hand with the trigger accessible to the user's hand while gripping the handheld member, e.g., actuated by the physician's thumb, actuated by a user's index finger (for instance, with a gun-like trigger), etc. The trigger may, for example, be configured to couple to the interior elongated member or hollow elongated member. It should be appreciated that an electrical circuit can be created to actuate the mechanical translation of the interior elongated member or hollow elongated member.

Upon activation of the trigger, the retention interface is decoupled from the sinus dilator. For example, the interior elongated member may be relatively displaced with respect to the hollow elongated member. In some embodiments, the relative displacing of the interior elongated member with respect to the hollow elongated member includes proximally displacing the retention interface within the hollow elongated member while the hollow elongated member remains in a substantially fixed position relative to the handheld member. For example, the actuation of the trigger may cause the retention interface to displace such that at least a portion of the retention interface that is outside of the distal end of the hollow elongated member is displaced proximally within the hollow elongated member. In some instances, the distal tip of the hollow elongated member may provide a stop against which the sinus dilator is pulled against as all or part of the retention interface is displaced proximally within the hollow elongated member. In some cases, actuation of trigger in the embodiments described above decouples the sinus dilator from the insertion device as the retention interface is displaced proximally with respect to the hollow elongated member.

In other embodiments, the relative displacing of the interior elongated member with respect to the hollow elongated member includes distally displacing the retention interface within the hollow elongated member while the hollow elongated member remains in a substantially fixed position relative to the handheld member. For example, the actuation of the trigger may cause the retention interface to displace such that at least a portion of the retention interface that is inside of the distal end of the hollow elongated member is displaced distally within the hollow elongated member. In some instances, the distal tip of the interior elongated member may push against the sinus dilator as the retention interface is displaced distally within the hollow elongated member. In some cases, actuation of the trigger in the embodiments described above decouples the sinus dilator from the insertion device as the distal tip of the interior elongated member is displaced distally with respect to the hollow elongated member.

The overall weight of the insertion device may take into account usability as a handheld device by the user, e.g., to permit a physician to easily hold and handle the device during an insertion procedure. The shape of the handheld member may vary, but in some instances may be in the shape of a wand with a button or switch trigger, a gun-like handle and trigger, or other graspable and usable shape.

As summarized above, the insertion device is dimensioned such that at least the distal end of the device can pass through the nasal cavity of a subject. The distal end may include, for example, at least a portion of the hollow elongated member, interior elongated member and retention interface. As such, at least the distal end of the device has a cross-sectional diameter that is 10 mm or less, such as 8 mm or less, and including 5 mm or less. The elongated members may have the same outer cross-sectional dimensions (e.g., diameter) along its entire length. Alternatively, the cross-sectional diameter may vary along the length of the elongated members.

Furthermore, the lengths of the hollow elongated member and interior elongated member may vary. For example, the lengths of the elongated members may vary depending on the specific sinus being targeted. In some instances, the lengths of the elongated members range from 1 cm to 20 cm, such as 2 cm to 15 cm, including 5 cm to 10 cm. It should be appreciated that in some instances the hollow elongated member and interior elongated member may have different lengths from one another.

As stated above, the hollow elongated member and interior elongated member of the insertion device has a proximal end and a distal end. The term "proximal end", as used herein, refers to the end of the elongated members (or the insertion device or other component on the insertion device) that are nearer the user (such as a physician operating the device in an insertion procedure), and the term "distal end", as used herein, refers to the end of the elongated members (or the insertion device or other component on the insertion device) that are nearer the target stenotic opening of the subject during use.

The hollow elongated members may be, for example, a structure of sufficient rigidity to allow the distal end to be pushed through tissue when sufficient force is applied to the proximal end of the device. As such, in some embodiments, the elongated member is not pliant or flexible, at least not to any significant extent. Example materials may include, but are not limited to, metals, metal alloys (e.g., stainless steel), polymers such as hard plastics, etc.

In some embodiments, the hollow elongated member includes a curved tip section at its distal end. The curvature and length of curvature may vary in degree, and may vary according to application, such as with which sinus opening is being accessed, e.g., maxillary sinus, frontal sinus, sphenoid sinus, etc. In some embodiments, to facilitate access to an opening of the maxillary sinus, the curved tip section is configured to bend at an angle ranging from 0° to 150°, such as 10° to 130°, including 20° to 120°, or 30° to 120°, or 60° to 120°, or 90° to 120°, or 100° to 120°, or 105° to 115° from the axis of the non-curved portion of hollow elongated member. In some embodiments, the curved tip section is configured to bend at an angle ranging from 105° to 115°, such as 110°, from the axis of the non-curved portion of hollow elongated member. In some cases, the length of the curved tip section (e.g., the arc length of the curved tip section) is 5 cm or less, such as 3 cm or less, including 2 cm or less, or 1 cm or less, or 0.5 cm or less. As such, in the above embodiments, when the sinus dilator is coupled to the insertion device, the sinus dilator may be positioned at an angle relative to the hollow elongated member of the insertion device. For instance, the longitudinal axis of the sinus dilator may be at an angle relative to the longitudinal axis of the hollow elongated member. The angle may be in the ranges and values described above.

The interior elongated member may be, in some instances, a structure of sufficient rigidity to allow the sinus dilator to be pushed through the stenotic opening when sufficient force is applied to the proximal end of the device, even when the stenotic opening is completely occluded. In some instances, the interior elongated member may be a metal, metal alloy, polymer (hard or pliant and flexible), etc. Further, the interior elongated member is, in some instances, a structure sufficiently pliant and flexible such that the interior elongated member may be relatively displaced in a hollow elongated member having a curved tip section. Examples of sufficiently pliant and flexible materials may include, but are not limited to, polymers such as plastics, rubber-like polymers, flexible metal (e.g., flexible wire), etc. In such cases, the hollow elongated member may provide the rigidity necessary to push the sinus dilator through the stenotic opening with sufficient force applied to the proximal end of the device.

As summarized above, the interior elongated member may include a retention interface adapted to removably couple to the sinus dilator. For example, the retention interface may be configured to mate with (e.g., slide within), clamp on, or removably couple in another way with, the sinus dilator. In some instances, the retention interface is part of the interior elongated member in that the retention interface and interior elongated member are parts of a single unitary piece of material. In other instances, the retention interface may be a separate piece of material that is coupled to the interior elongated member, either removably or non-removably coupled in different embodiments. Retention interfaces that are removably coupled to the interior elongated member may provide the ability to replace retention interfaces (e.g., for sanitation purposes, or replacement purposes) or switch to different types of retention interfaces (e.g., for use with different types or sized sinus dilators).

In some embodiments, the retention interface is adapted to fit within a central passageway of the sinus dilator. The sinus dilator may be, for example, shaped and sized to fit within the contours of the central passageway of the sinus dilator. The sinus dilator may then be coupled to the retention interface by sliding the sinus dilator onto the retention interface. In some instance, the shape and size of the retention interface matches the contours of the central passageway of the sinus dilator.

Also, in some instances, the interior elongated member may be slid all the way through the central passageway of the sinus dilator with a tip portion extending out of the sinus dilator.

In some aspects, the insertion device is configured to stop the sinus dilator when it is completely slid onto the retention interface so that the dilator cannot continue to slide down the retention interface and interior elongated member. In some instances, the retention interface is shaped to stop the sinus dilator when completely slid on the retention interface, e.g., shaped to include stops. For example, the retention interface may be shaped with a decreasing cross-sectional width closer to the tip. Since the retention interface is shaped and sized to fit with the interior surface of the central passageway of sinus dilator, the retention interface may be adapted to abut one or more contact surfaces on the sinus dilator, acting as stops for the sinus dilator when completely inserted on the retention interface. Thus, the stops prevent the sinus dilator from being inserted further once the stops are encountered. The stops may provide addition support when force is applied from the proximal end of the insertion device in order to push the sinus dilator through tissue and a stenotic opening. Furthermore, such stops do not inhibit movement of the retention interface in the opposite direction back out the central passageway of the sinus dilator, to allow for decoupling of the retention interface and the sinus dilator. In some instances, the interior elongated member has a wider cross sectional width than the retention interface such that the wider cross sectional width functions as a stop against a corresponding contacting surface on the sinus dilator. In some instances, the sinus dilator may abut the hollow elongated member when inserted completely on the retention interface. The hollow elongated member may, in such case, function as a stop in place of, or in addition to, any stops provided on the retention interface or interior elongated member.

In some embodiments, the retention interface includes retaining elements that provide an additional securing force to the sinus dilator so that it may not slide back off the retention interface unless a sufficient amount of force is applied to overcome the additional securing force, or until the additional securing force is removed. For example, the retention interface may be adapted to provide an outward force on the central passageway of the sinus dilator, thus providing an outward force on the central passageway which helps retain the sinus dilator coupled to the retention interface. The retention interface may, for instance, include a compressible lip, bump, or other protrusion that is compressed when inserted within the central passageway of the sinus dilator, providing the outward force on the central passageway. Other retaining elements may also be used, e.g., lips, bumps or protrusion that fit within mating recesses on the sinus dilator that "snap" the dilator onto the retention interface. In some instances, the distal tip of the retention interface is split (e.g., in a polymer flexure design), with each arm of the split tip stressed or flexed inward towards one another when inserted within the central passage way of the sinus dilator. In such case, for example, the arms of the split tip have a tendency to return to their unstressed or not flexed position, thus providing the outward force to the interior of the central passageway of the sinus dilator.

Sufficient force to overcome the additional securing force by the retaining elements may be provided by, for example, withdrawing the interior elongated member while the sinus dilator is securely fit within the stenotic opening. As another example, the sufficient force may be provided by the hollow elongated member being displaced and pushed into the sinus dilator to push the sinus dilator off the retention interface.

Additionally, the distal tip of the retention interface, whether split or not, may include a small lip, bump, or other protrusion that functions as a retaining element to provide the additional securing force necessary to resist the sinus dilator from moving back off the retention interface. It should be appreciated that the size and shape of the protrusions will determine the amount of sufficient force necessary to overcome the additional securing force provided by the protrusions.

It should also be appreciated that the above described retaining elements are exemplary and that other types of retaining elements may be implemented. It should also be appreciated that the retaining element described above, and equivalents thereof, serve as means for providing an additional securing force to the sinus dilator when inserted on the retention interface.

In some embodiments, the insertion device may include a lumen that extends to the distal end of the insertion device. For example, the lumen may extend within the interior elongated member and include an opening at the distal tip of the elongated member. It should be appreciated that the lumen may, in some instances, be formed by the interior elongated member or formed by a tube positioned within the interior elongated member. In alternative embodiments, the lumen may be positioned within the hollow elongated member but not within the interior elongated member.

In some instances, insertion device is configured to couple the lumen to a fluid source to dispense fluid into the sinus cavity or nasal cavity before, during or after placement of the sinus dilator in the stenotic opening. The term "fluid" is used herein generally to refer to any variety of fluids, mists, gels, single or multi-phase liquid, etc., or combinations thereof. The fluid source may be located in various positions, depending on design, e.g., being located on or in the device, attaching to the device (e.g., a cartridge, etc.), or coupling to the device via a connection port, etc. In some instances, the lumen is coupled to a hollow tube in the handheld member that brings the lumen in fluid communication with the fluid source. Example fluids that may be dispensed are, for example, fluids comprising water, saline solution, drugs, etc. Example drugs that may be present in the fluid (e.g., in fluid or solid form) may include, but are not limited to fluids comprising one or more analgesics, anesthetics, anti-inflammatories, antibiotics, steroids, drugs that control or limit bleeding (e.g., vasoconstrictors), etc.). Vasoconstrictors may include, for example, oxymetazoline, epinephrine, tranexamic acid, salts thereof, combinations thereof, and the like.

In some embodiments, the lumen may be coupled to a pellet source or other source of solid, such as powder, etc. In such case, the lumen is used to dispense solid pellets, for example, into the sinus cavity and/or nasal cavity before, during or after placement of the sinus dilator in the stenotic opening. Furthermore, in some instances, the lumen may be coupled to a suction source (e.g., vacuum source) in order to provide suctioning, in order to remove fluid, tissue debris, etc. It should be appreciated that in some instances more than one lumen may be implemented. For example, in some instances, one lumen may be provided to dispense fluids while another lumen is provided for suctioning purposes.

In some embodiments, the insertion device may be configured to include a camera positioned near the distal end of the hollow elongated member in order to assist in visualizing the stenotic site, nasal cavity, or sinus cavity. In some instances, the camera may be positioned on the exterior surface of the hollow elongated member and, for example, electrically coupled to a monitor via an electrical wire extending along or within the hollow elongated member. In other instances, the camera may be positioned within the hollow elongated member. For example, a camera may be positioned at the tip of the interior elongated member and electrically coupled to a monitor via an electrical wire extending within the interior elongated member.

The insertion device, or components thereof, may be configured for one time use (i.e., disposable) or may be re-usable, e.g., where the components are configured to be used two or more times before disposal, e.g., where the device components are sterilizable.

Additional aspects of the insertion devices and methods for use are described in more detail in U.S. patent application Ser. Nos. 13/219,505 and 13/219,497, both filed Aug. 26, 2011, the disclosures of each of which are incorporated herein by reference.

Additional Aspects of the Sinus Dilator and Insertion Device

Referring now to FIG. 1, there is shown a human patient 10 having two frontal sinuses (FS) and two maxillary sinuses (MS). Each of these four sinuses has an opening which can be accessed by way of the patient's nostrils. The openings include maxillary sinus openings 11 and 12, of which opening 11 is shown in a normal open condition and opening 12 shown in an occluded or stenotic condition. Similarly, the patient 10 has frontal sinus openings 13 and 14, of which opening 14 is shown in a normal open condition and opening 13 is shown in an occluded or stenotic condition.

Figure 2:
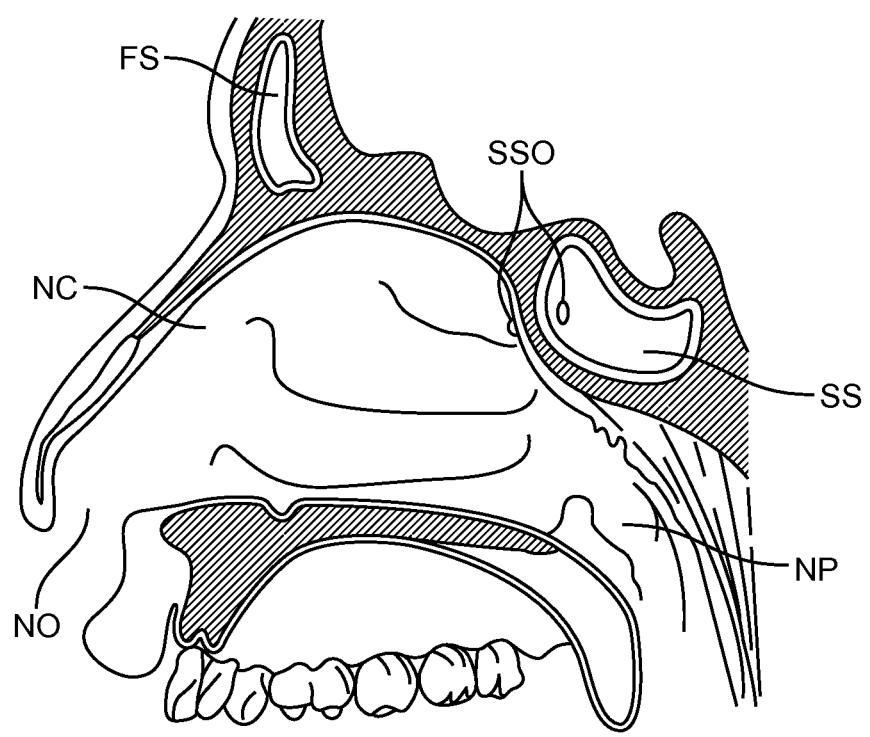
FIG. 2 is a sectional view of a portion of a human head showing the positions of the frontal sinus (FS) and the sphenoid sinus (SS)

Referring now to FIG. 2, there is shown a sectional view of a patient's nose and sinuses including the nasal cavity (NC), the nasopharynx (NP), the nostril opening (NO), the frontal sinus (FS), the sphenoid sinus (SS) and the sphenoid sinus opening (SSO).

Additional aspects of the sinus dilator and the insertion device will now be described in more detail in the following sections.

In Situ Osmotic Anchor

In certain embodiments, the sinus dilator includes two drivers, such as a first driver and a second driver. The first driver may be positioned proximal to the second driver, such that the second driver is positioned closer to the distal end of the sinus dilator than the first driver (e.g., the first driver may be termed the "proximal driver" and the second driver may be termed the "distal driver"). In certain embodiments, the first and second drivers are self-expanding drivers, such as self-expanding osmotic drivers. As such, the first and second drivers may include an osmotically active agent and an osmopolymer.

In certain embodiments, the second driver is configured to have a faster rate of expansion than a rate of expansion of the first driver. In some instances, the second driver is configured to have a duration of expansion less than a duration of expansion of the first driver. A second driver configured as described above, may facilitate the prevention of the device from being squeezed out of the stenotic opening and into the nasal cavity during device expansion.

In some instances, the first and second drivers have different compositions of the osmotically active agent and/or the osmopolymer. For example, the first and second drivers may have different concentrations of the osmotically active agent (or different osmotically active agents). In some cases, the first and second drivers may have different concentrations of the osmopolymer (or different osmopolymers). A sinus dilator that has different first and second driver compositions may facilitate retention of the sinus dilator in the stenotic opening during use. For example, the device may be retained in the stenotic opening such that the sinus dilator is not expelled out of the stenotic opening and into the nasal cavity during device expansion.

For example, in embodiments where the first and second drivers include the same osmotically active agent, the second driver (e.g., distal driver) may include a greater concentration of osmotically active agent than the first driver (e.g., proximal driver). Inclusion of a greater concentration of osmotically active agent in the second driver may cause the second driver to expand at a greater rate than the first driver. In some instances, if the second driver includes a greater concentration of osmotically active agent than the first driver, the second driver also includes a lower amount of osmopolymer than the first driver. In certain embodiments, the relatively high osmotically active agent concentration and relatively low osmopolymer amount of the second driver relative to the first driver causes the second driver to expand more rapidly than the first driver (e.g., due to the higher osmotically active agent concentration), and after expansion causes the second driver to collapse back down in size more rapidly than the first driver (e.g., because the second driver has less osmopolymer to keep it fully expanded). In these embodiments, the second driver expands more rapidly than the first driver, and thus anchors the sinus dilator in the stenotic opening (e.g., prevents the sinus dilator from being expelled into the nasal cavity). In some cases, the duration of expansion of the second driver is less than that of the first driver, such that the anchoring effect of the second driver is temporary. In these embodiments, the sinus dilator may be more easily removed after the second driver has decreased in size relative to its fully expanded configuration.

Thus, in certain embodiments, the second driver is configured to have (i) a faster rate of expansion than a rate of expansion of the first driver, and (ii) a duration of expansion less than a duration of expansion of the first driver, whereby the second driver prevents the device from being expelled out of the stenotic opening and into the nasal cavity during device expansion.

In certain embodiments, the second driver is configured to have a duration of expansion of 8 hours or less, such as 6 hours or less, or 4 hours or less, or 2 hours or less, or 1 hour or less, or 0.5 hours or less. In some cases, the second driver is configured to have a duration of expansion of 2 hours or less. In certain embodiments, the first and second drivers are configured such that the duration of expansion of the second driver ranges from 0.5 to 12 hours less than the duration of expansion of the first driver, such as 0.5 hours to 10 hours less, including 0.5 hours to 8 hours less, or 0.5 hours to 6 hours less, or 0.5 hours to 4 hours less, or 1 hours to 4 hours less than the duration of expansion of the first driver.

As described above, the second driver may expand at a greater rate than the first driver, but may not stay in a fully expanded configuration for as long as the first driver. In certain embodiments, the second driver is configured to have a diameter greater than the diameter of the first driver during a period of stenotic opening dilation, and the second driver is configured to have a diameter less than the diameter of the first driver following said period of stenotic opening dilation. For example, the period of stenotic opening dilation may be 0.5 hours or more, such as 1 hour or more, including 1.5 hours or more, or 2 hours or more. In some cases, the period of stenotic opening dilation is 0.5 hours or more. In some instances, the period of stenotic opening dilation is 2 hours or less, such as 1.5 hours or less, or 1 hour or less, including 0.5 hours or less. For example, the period of stenotic opening dilation may be 2 hours or less.

In certain embodiments, each of the first and second drivers includes an osmotically active agent, the second driver having a concentration of the osmotically active agent that is greater than that in the first driver. In some cases, the osmotically active agent in the second driver has a concentration of 50 to 90 wt %, such as 50 to 80 wt %, including 50 to 70 wt %. In some instances, the osmotically active agent in the first driver has a concentration of 10 to 50 wt %, such as 20 to 50 wt %, including 30 to 50 wt %. In certain cases, the osmotically active agent in the second driver has a concentration of 50 to 70 wt % and the osmotically active agent in the first driver has a concentration of 30 to 50 wt %.

In certain embodiments, each of the first and second drivers includes an osmopolymer, the second driver having a concentration of the osmopolymer that is less than that in the first driver. In some cases, the osmopolymer in the first driver has a concentration of 30 to 70 wt %, such as 30 to 80 wt %, including 30 to 90 wt %. In certain instances, the osmopolymer in the second driver has a concentration of 10 to 50 wt %, such as 20 to 50 wt %, including 30 to 50 wt %. In some cases, the osmopolymer in the first driver has a concentration of 30 to 70 wt % and the osmopolymer in the second driver has a concentration of 20 to 50 wt %.

Figures 4, 5:
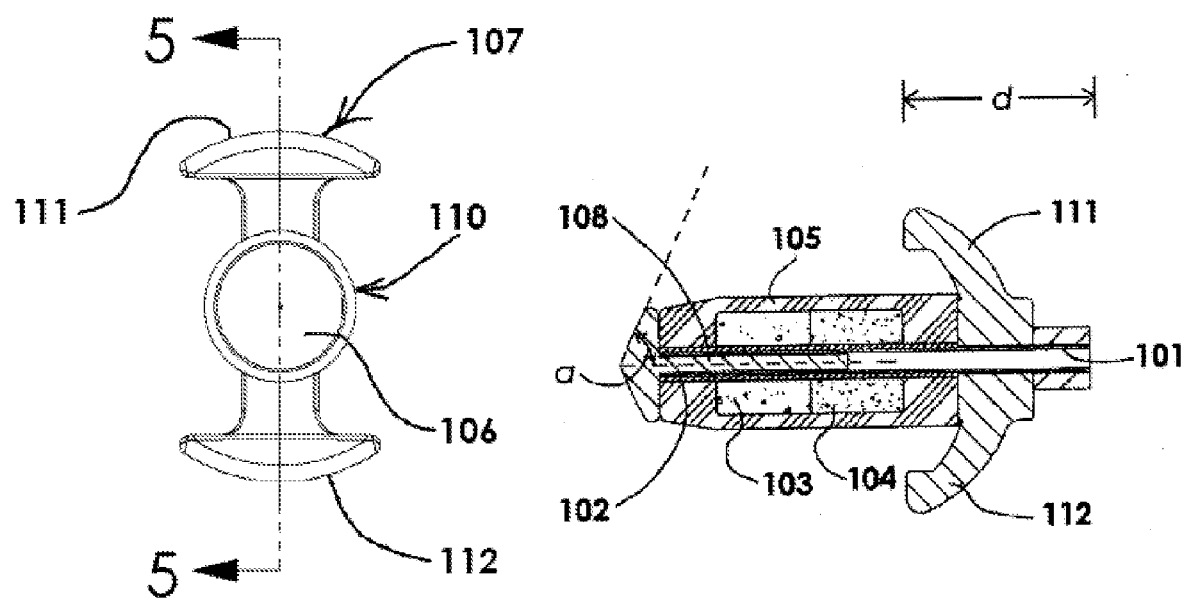
FIG. 4 is an end view of the device shown in FIG. 3.
FIG. 5 is a sectional view of the device shown in FIGS. 3 and 4, taken along line 5-5.
Figure 7:
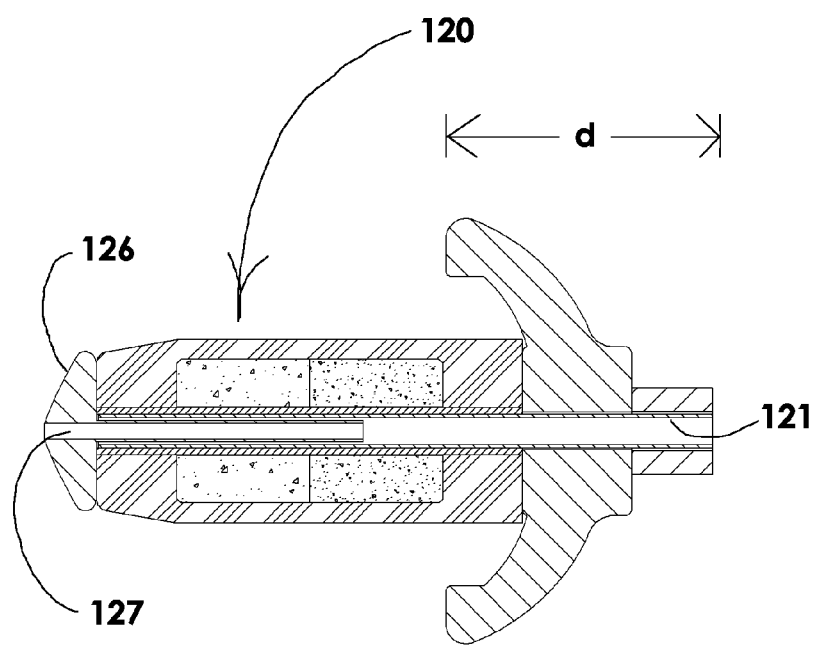
FIG. 7 is a sectional view of the device shown in FIG. 6, taken along line 7-7.

In some aspects, an osmotic driver element is designed to operate in concert with a mechanical proximal anchor to anchor a sinus dilator within a sinus opening during dilation. As illustrated in FIGS. 5 and 7, the dilators 100 and 120 each have a pair of annularly shaped osmotic tablets 103, 104 positioned side-by-side in direct contact with one another, and which are both completely enclosed within the elastic semipermeable membrane 105. The compositions of the osmotic tablets are selected such that when the membrane 105 is exposed to aqueous body fluids, one of the osmotic tablets 103, 104 imbibes water across the semipermeable membrane 105 causing it to radially expand at a different rate than the adjoining osmotic tablet. The osmotic tablet 104 located closer to the proximal end of the device 100 is formulated to have a slower radial expansion rate than the osmotic tablet 103 positioned closer to the distal end of the device 100 by selecting the osmotic composition within the tablets 103, 104 to be different from each other. Typically, the tablets 103, 104 are formulated primarily with an osmotic agent (e.g., a water soluble salt such as NaCl) and an osmopolymer, such as a hydrogel-forming osmopolymer (e.g., an osmopolymer that forms a hydrogel when exposed to water). In this aspect, the proximal tablet 104 is made with a lower osmotic agent content and a higher hydrogel polymer content than the distal tablet 103. For example, the proximal tablet 104 may contain from 35 to 65 wt % osmotic agent and 30 to 60 wt % osmopolymer; and the distal tablet 103 may contain from 45 to 75 wt % osmotic agent and 20 to 50 wt % osmopolymer. The net effect of this compositional difference is to create in situ a tapered shape of osmotic driver 110 as the driver expands. The tapered shape results from the distal tablet 103 imbibing water more quickly than proximal tablet 104 and thereby expanding to a larger diameter than the diameter of the proximal tablet 104. In the case of a maxillary sinus dilation, the length of the maxillary sinus opening 11 (length is the distance from the nasal passageway side to the maxillary sinus cavity side) is typically about 1 to 3 mm. Since the length of the sinus opening is much less than the combined length of the tablets 103, 104, at least a portion of the distal tablet 103 is positioned within the sinus cavity (MS) during use. The resulting expansion of tablets 103, 104 forms a wedge with the larger diameter tablet 103 being positioned within the sinus cavity (MS) while the smaller diameter tablet 104 is within the sinus opening 11. The resulting wedge shape helps prevent the device 100 from being squeezed out of the sinus opening 11 and into the nasal passageway 15 during dilation. During dilation, as the tablets 103, 104 expand radially outwardly, the tapered configuration of the membrane causes the dilator 100 to be forced in the opposite direction to the directional force exerted by the proximal mechanical anchor 107. The two opposing forces thereby retain the dilator 100 within the sinus opening 11. This differential swelling is achieved by selecting the concentration of osmotic agent within the distal tablet 103 to be at least 10% greater than the concentration of osmotic agent in the proximal tablet 104.

Wicking Agent

In certain embodiments, the osmotic driver of the sinus dilator includes a wicking agent. In some cases, the wicking agent is configured to increase the rate of expansion of the osmotic driver, as compared to a sinus dilator that does not include a wicking agent. For example, the wicking agent may absorb fluid from the surrounding environment or tissues during use of the sinus dilator. As such, in certain instances, the wicking agent is configured to decrease the amount of time for the sinus dilator to expand from the non-expanded configuration to the expanded configuration, as compared to a sinus dilator that does not include a wicking agent.

In certain embodiments, the wicking agent includes an absorbent compound. In some cases, the wicking agent includes hydroxypropyl cellulose; chemically cross-linked organic polymers, such as cross-linked sodium carboxymethyl cellulose, cross-linked polyvinyl pyrrolidone; physically cross-linked organic polymers, such as microcrystalline cellulose and powdered cellulose; inorganic swelling agents, such as bentonite clay; combinations thereof; and the like. In certain instances, the wicking agent includes hydroxypropyl cellulose.

In some embodiments, the wicking agent has an average particle size of 1000 µm or less, such as 750 µm or less, including 500 µm or less, or 250 µm or less, or 100 µm or less, or 50 µm or less, or 25 µm or less, or 10 µm or less, or 1 µm or less. In some cases, the wicking agent has an average particle size of 50 µm or less.

In accordance with another aspect, a wicking agent can be incorporated into the osmotic tablets 103, 104 of the sinus dilator 100 to promote water transmission across the membrane 105 and enhance the rate of expansion of osmotic driver 110. The use of a wicking agent is particularly useful for short term dilations (e.g., dilation times of up to about 2 hours duration), e.g., where the patient does not leave the doctor's office while the device 100 is in use. The wicking agent functions by capillary action to conduct water that has passed through the membrane 105 and into the osmotic tablet 103, 104. In certain embodiments, the tablets 103, 104 contain from 10 to 50 wt % of the wicking agent. In other embodiments, the tablets 103, 104 contain from 15 to 30 wt % of the wicking agent. In one embodiment, the wicking agent is micronized (~300 mesh) low (11%) substituted hydroxypropyl cellulose (L-HPC 31) supplied by Shin-Etsu Chemical Co., Ltd., Tokyo, Japan. Other suitable wicking agents include chemically cross-linked organic polymers, such as cross-linked sodium carboxymethyl cellulose (Ac-di-Sol; FMC Corp., Philadelphia, Pa.), and cross-linked polyvinyl pyrrolidone (PVP-XL; International Specialty Products, Wayne, N.J.); physically cross-linked organic polymers, microcrystalline cellulose (FMC Corp., Philadelphia, Pa.), and powdered cellulose (Solka-Floc; International Fiber Corp., North Tonawanda, N.Y.), inorganic swelling agents, such as bentonite clay; combinations thereof; and the like.

Insertion Device Circumferential Trigger

As described above, an insertion device for a sinus dilator may include a trigger, where actuation of the trigger decouples the sinus dilator coupled to the distal end of the insertion device. In certain embodiments, the trigger is configured to be accessible to the user from any gripping position as the user holds the insertion device during use. For example, the insertion device may be rotated about its longitudinal axis to any angle relative to the user's hand, and the trigger may be maintained in a convenient position for actuation by the user. In some cases, to facilitate actuation of the trigger from any hand position as described above, the insertion device includes a trigger that extends around the exterior surface of the handle of the insertion device. For instance, the trigger may extend around 25% or more of the exterior surface of the handle, such as 50% or more, or 75% or more. In some cases, the trigger extends substantially entirely around the exterior surface of the handle. For example, the trigger may extend completely around the circumference of the exterior surface of the handle. As such, the insertion device may be rotated about its longitudinal axis to any angle relative to the user's hand, and the trigger will be in a convenient position for actuation by the user.

Aspects of the insertion device include a handheld member including (i) a handle sized to be grasped by a user's hand and having a grippable exterior surface; and (ii) a trigger activated by a user's thumb or finger. A hollow elongated member is coupled at its proximal end to the handheld member. The hollow elongated member has a distal end having an opening to an interior cavity of the hollow elongated member and a retention interface for removably coupling to a sinus dilator. The device includes an interior elongated member extending within the interior cavity of the hollow elongated member and operatively connected to the trigger.

In certain embodiments, the trigger extends around 25% or more of the exterior surface of the handle, such as 50% or more of the exterior surface of the handle, including 75% or more of the exterior surface of the handle, or around the entire exterior surface of the handle. In some cases, the handle has a circular cross-section and the trigger extends around a percentage of a circumference of the handle, such as 25% of the circumference of the handle, including 50% of the circumference of the handle, or 75% of the circumference of the handle, or around the entire circumference of the handle.

In accordance with another aspect, and as shown in FIGS. 10 and 12 to 16, the insertion device 200 has a trigger 203 that extends around the entire circumference of handle 202. While device 200 has a handle 202 with a circular cross section, those skilled in the art will appreciate that handle 202 can have other cross sectional shapes, including oval, square, etc. The advantage of trigger 203 is that the device 200 can be gripped from any side and the trigger 203 will be conveniently located for actuation by the user's thumb or finger. While trigger 203 is shown as extending completely around the exterior surface of the handle 202, other embodiments of trigger can extend over a lesser portion of that circumference. In certain embodiments, the trigger 203 can extend around 25% or more of the outer surface of handle 202. In other embodiments, the trigger 203 can extend around 50% or more of the outer surface of handle 202. In other embodiments, the trigger 203 can extend around 75% or more of the outer surface of handle 202.

Insertion Device with Low Profile Tip

In some embodiments, the insertion device is configured to facilitate insertion of a sinus dilator into a stenotic opening in a subject. For example, the insertion device (e.g., the distal end of the insertion device) may be sized to fit within the nasal cavity of a subject. As described above, the sinus dilator may be positioned at an angle relative to the hollow elongated member of the insertion device (e.g., at an angle ranging from 105° to 115°, such as 110°). As such, the insertion device may be configured to minimize the overall width of the device during use. For instance, the distance (h) between the distal tip of the sinus dilator and the opposite outer surface of the hollow elongated member of the insertion device (see FIG. 19) may be minimized to facilitate insertion of the sinus dilator in the nasal cavity of a subject.

As described above, the insertion device includes a handheld member including a handle and a trigger. The insertion device also includes a hollow elongated member having a proximal end coupled to the handheld member. As described above, in certain embodiments, the insertion device also includes an interior elongated member coupled to the trigger and extending within a central passageway of the hollow elongated member.

In certain embodiments, the hollow elongated member is coupled at its distal end to a retention tip. The retention tip may be configured to removably couple to a sinus dilator, as described in more detail below. In certain embodiments, the retention tip includes an interior cavity, such as a central passageway. The central passageway of the retention tip may be in fluid communication with the central passageway of the hollow elongated member. In some instances, the retention tip includes an opening to the central passageway of the hollow elongated member. As such, the central passageway of the hollow elongated member may be in fluid communication with the central passageway of the retention tip.

In certain embodiments, the retention tip is angularly coupled to the distal end of the hollow elongated member with respect to the central passageway of the hollow elongated member. In these embodiments, the central passageway of the retention tip is non-collinearly aligned with the distal end of the hollow elongated member. For instance, the retention tip may be coupled to the distal end of the hollow elongated member at an angle with respect to a longitudinal axis of the hollow elongated member. In certain cases, the angular coupling between the retention tip and the hollow elongated member is such that the longitudinal axis of the hollow elongated member is at an angle with respect to the longitudinal axis of the retention tip. In some instances, the angular coupling between the hollow elongated member and the retention tip has an angle that is less than 180°, such that the angle between the longitudinal axis of the hollow elongated member and the longitudinal axis of the retention tip is less than 180°. For example, the angular coupling between the hollow elongated member and the retention tip may have an angle from 0° to 150°, such as 10° to 130°, including 20° to 120°, or 30° to 120°, or 60° to 120°, or 90° to 120°, or 100° to 120°, or 105° to 115°. In some embodiments, the angle ranges from 105° to 115°, such as 110°.

In embodiments where the retention tip is angularly coupled to the hollow elongated member as described above, the hollow elongated member may be substantially linear. For example, the distal end of the hollow elongated member may be substantially linear. In certain instances, the distal end of the hollow elongated member does not include a curved tip section as described in some of the alternate embodiments described above.

In certain embodiments, the retention tip is coupled to the distal end of the hollow elongated member at a position between the proximal and distal ends of the retention tip. For example, the retention tip may be coupled to the distal end of the hollow elongated member on a side of the retention tip. In some instances, the retention tip is not coupled to the distal end of the hollow elongated member at the proximal end of the retention tip.

In certain embodiments, to minimize the overall width of the insertion device (e.g., the distal end of the insertion device), the retention tip has a length (e.g., as measured along its longitudinal axis) that is 15 mm or less, such as 10 mm or less, including 7 mm or less, or 5 mm or less, or 3 mm or less, or 1 mm or less.

The sinus dilator may be coupled to the retention tip (e.g., slid in, snapped in, clamped, etc.) and then the distal end of the insertion device may be inserted within the nasal cavity to position the sinus dilator within the stenotic opening. In certain embodiments, the retention tip and sinus dilator are configured to be removably coupled, thus the sinus dilator may be decoupled from the insertion device and left within the stenotic opening. The retention tip may include various coupling mechanisms to retain the sinus dilator coupled to the insertion device. In some instances, the retention tip is sized and shaped to fit around at least a portion of the proximal end of the sinus dilator, thus retaining the sinus dilator on the insertion device. The retention tip may provide sufficient retention to maintain the sinus dilator coupled while permitting some light axial and off-axis loads or bending moments. In some instances, the sinus dilator is sufficiently rigidly affixed to the retention tip to enable a user (e.g., physician) to push the sinus dilator through a stenotic opening even when the opening is completely shut.

As described above, in certain embodiments, the retention tip includes an opening to the central passageway of the hollow elongated member. As such, the central passageway of the hollow elongated member is in fluid communication with the central passageway of the retention tip. The distal end of the retention tip may include an opening configured to accept the distal end of the sinus dilator, for example to facilitate retention of the sinus dilator on the insertion device. In certain embodiments, the opening between the retention tip and the hollow elongated member is sized to allow passage of the distal end of the interior elongated member through the opening. In some cases, the distal end of the interior elongated member is configured to extend through the opening in the retention tip into an interior cavity of the retention tip. In these embodiments, the distal end of the interior elongated member may be displaced distally and/or proximally within the opening between the retention tip and the hollow elongated member.

In certain embodiments, the distal end of the interior elongated member is configured to couple to the sinus dilator to facilitate retention of the sinus dilator on the insertion device. For example, the distal end of the interior elongated member may include a retention interface, as described in some embodiments above. In certain instances, the retention interface is sized and shaped to fit within the sinus dilator, e.g., within an opening in the sinus dilator, or recess, slot, and the like, for example in the side of the sinus dilator.

Upon activation of the trigger, the sinus dilator may be decoupled from the retention tip. For example, the interior elongated member may be relatively displaced with respect to the hollow elongated member. In some embodiments, the relative displacing of the interior elongated member with respect to the hollow elongated member includes proximally displacing the retention interface within the hollow elongated member while the hollow elongated member remains in a substantially fixed position relative to the handheld member. In some cases, the interior elongated member is configured to decouple from the sinus dilator when the interior elongated member is displaced proximally within the hollow elongated member. For example, the actuation of the trigger may cause the retention interface to displace such that at least a portion of the retention interface that was coupled to the distal end of the sinus dilator is displaced proximally within the hollow elongated member. In some instances, the retention interface is displaced sufficiently proximally within the hollow elongated member so that the sinus dilator is able to be decoupled from the insertion device.

In other embodiments, the relative displacing of the interior elongated member with respect to the hollow elongated member includes distally displacing the interior elongated member within the hollow elongated member while the hollow elongated member remains in a substantially fixed position relative to the handheld member. In certain instances, the interior elongated member is configured to decouple the sinus dilator from the retention interface when the interior elongated member is displaced distally within the hollow elongated member. For example, the actuation of the trigger may cause the interior elongated member to displace such that the distal end of the hollow elongated member is displaced distally within the hollow elongated member. In some instances, the distal end of the interior elongated member may push against the proximal end of the sinus dilator as the interior elongated member is displaced distally within the hollow elongated member. In some cases, actuation of the trigger in the embodiments described above decouples the sinus dilator from the insertion device as the distal end of the interior elongated member is displaced distally with respect to the hollow elongated member.

Figure 9:
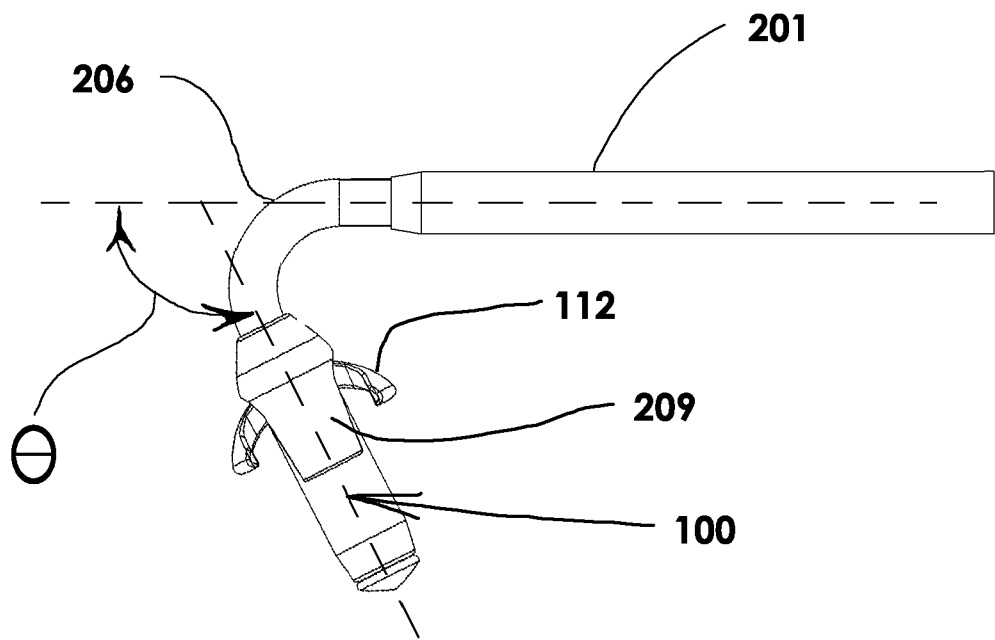
FIG. 9 is an enlarged view of the distal end of the insertion device.

An embodiment of an insertion device that includes a low profile tip as described above is shown, for example, in FIG. 19. For comparison, an alternative embodiment is shown in FIG. 9 described herein. In FIG. 9, the bend 206 in the distal tip of the insertion device accommodates the movement of the flexible rod 205 (see e.g., FIG. 14) which pushes the dilator 100 off of the distal end of the insertion device when the dilator is in position within the sinus opening. In certain embodiments, the bend 206 creates a larger height dimension to the distal tip of the insertion device as compared to an embodiment of an insertion device that includes a low profile tip. In certain instances, an insertion device that includes a low profile tip facilitates maneuvering the distal tip of the insertion device, with the dilator 100 mounted thereon, past the nasal turbinates and uncinate to reach a sinus opening (e.g., a maxillary sinus opening) for treatment.

Figure 19:
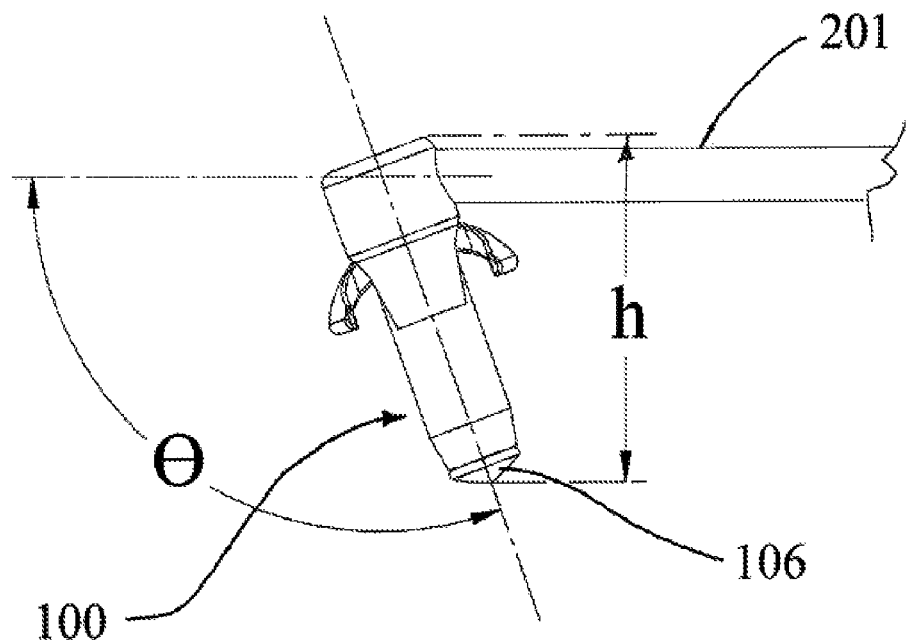
FIG. 19 is a side view of the distal end of an insertion device with a dilator mounted thereon, according to embodiments of the present disclosure.
Figure 20:
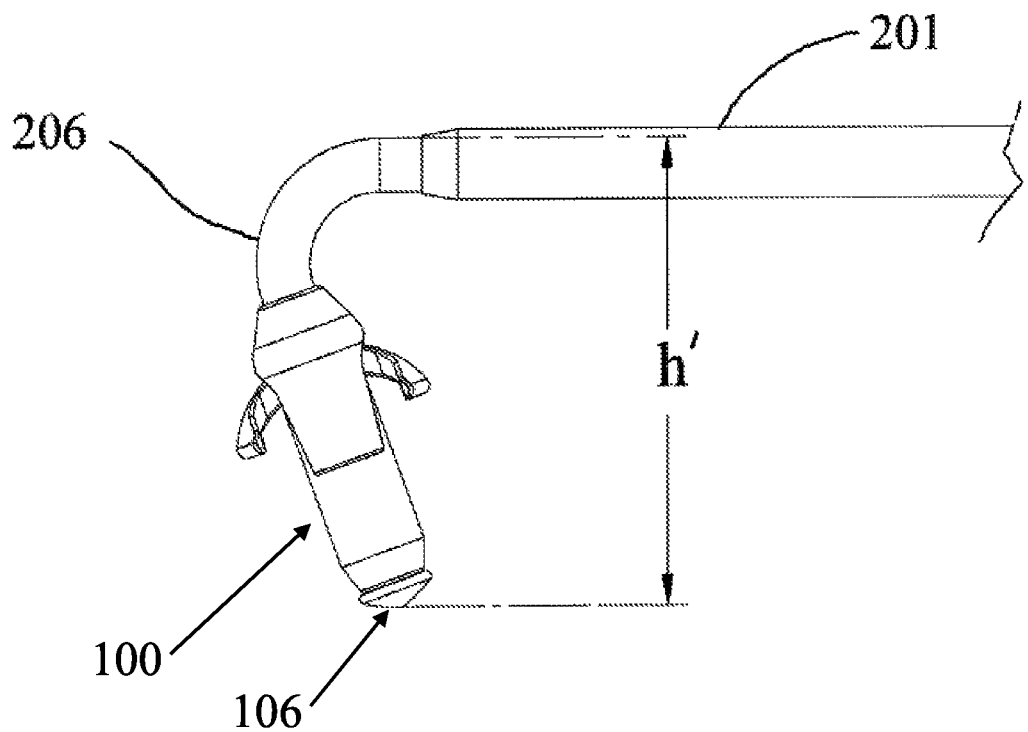
FIG. 20 is a side view of the distal end of the insertion device shown in FIG. 9.
Figure 21:
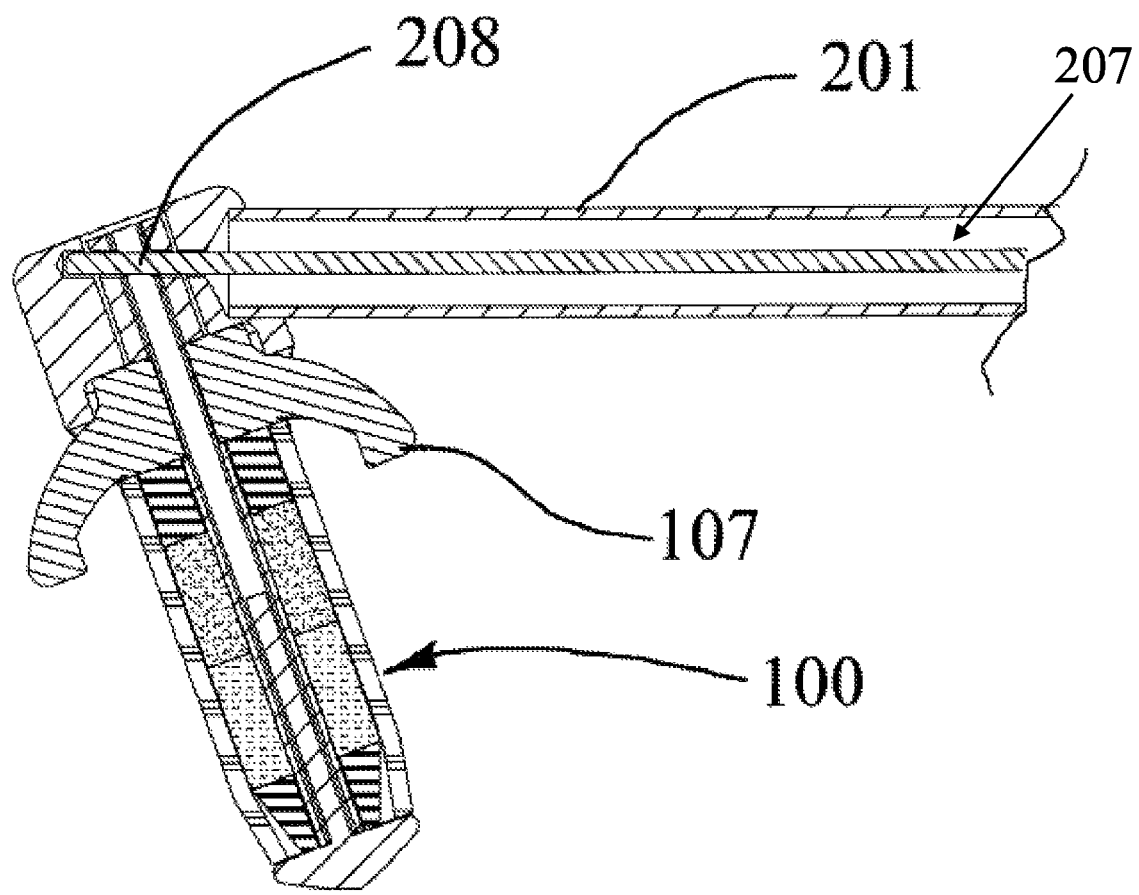
FIG. 21 is a sectional view of the insertion device and dilation device shown in FIG. 19.

An insertion device with a low profile distal tip is shown in side and sectional views in FIGS. 19 and 21, respectively. As a side-by-side comparison, FIG. 20 shows an insertion device with a curved distal tip (see e.g., FIG. 9) with a similar length sinus dilator mounted thereon. In all three of FIGS. 19 through 21, the dilator 100 has a length of 13.0 mm and is mounted so that the axis of the dilator 100 is at a 110° angle (θ) with respect to the axis of the hollow elongated member (e.g., cannula 201) of the insertion device. As shown in FIG. 19, the height (h) of the insertion device tip may be measured from the upper surface of the insertion device tip to the end of the distal tip 106 of the sinus dilator 100. As shown in FIG. 20, the height (h') of the insertion device tip is measured from the upper surface of the bend 206 to the end of the distal tip 106 of the sinus dilator 100. With a sinus dilator 100 having a length of 13 mm and mounted at an angle (θ) of 110°, the embodiments shown in FIG. 9 and FIG. 20 with the bend 206 have a height (h') of about 18 mm, whereas the height (h) of the insertion device shown in FIGS. 19 and 21 with the low profile insertion tip is about 13.5 mm. In certain embodiments, a smaller height of the distal tip of the insertion device with mounted sinus dilator 100 facilitates insertion of the sinus dilator into the maxillary sinus ostium through the nasal passageways and may provide greater flexibility for maneuvering the sinus dilator 100 into the correct orientation for insertion and deployment thereof in the sinus ostium.

As described above, in certain embodiments as shown in FIGS. 9 and 20, a flexible rod 205 (see e.g., FIG. 14) extends through the cannula 201, including through the bend 206, and abuts against the proximal end of the dilator 100. Once the dilator 100 is in position within a sinus opening, the flexible rod 205 is displaced distally by activation of the trigger 203, thereby pushing the dilator 100 off the tip of the insertion device. By comparison, in certain embodiments, the release of the dilator from the insertion device with a low profile tip may be performed in a different manner. As shown in FIGS. 19 and 21, a wire (or rod) 207 is coupled to the trigger (not shown) and extends from the distal tip of the insertion device. The distal end of wire 207 extends through a hole 208 in the proximal end of the dilator 100 and prevents the dilator 100 from sliding off the distal tip of the insertion device until the physician operates the trigger to displace the wire 207 in a proximal direction, this withdrawing the wire 207 from the hole 208. Once the wire is withdrawn from the hole 208, the dilator 100 can decouple from the distal end of the insertion device.

Figure 22:
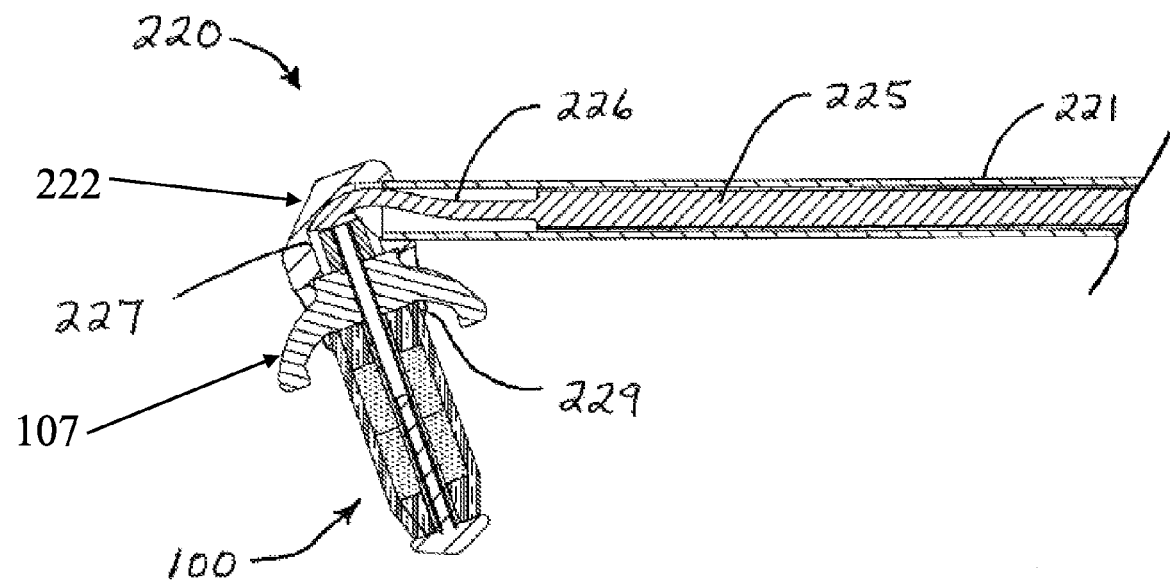
FIG. 22 is a sectional view of an insertion device with a dilator mounted thereon, according to embodiments of the present disclosure.
Figure 23:
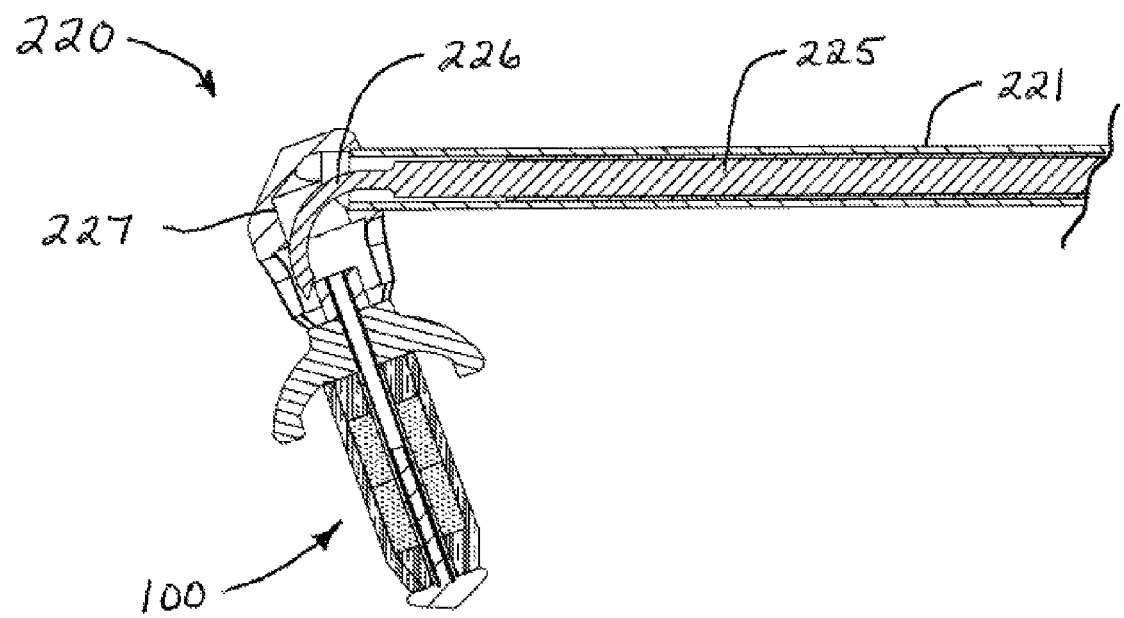
FIG. 23 is a sectional view of the insertion device and dilation device shown in FIG. 22, with the dilator deployed, according to embodiments of the present disclosure.

Turning now to FIGS. 22 and 23, there is shown an alternate embodiment of a low profile distal tip for insertion device 220. Insertion device 220 has a hollow elongated member (e.g., cannula 221) extending from a handle (not shown) with a trigger. Attached to the distal end of cannula 221 is a retention tip 222. As described above, the retention tip 222 may be attached to the distal end of the cannula 221 at an angle, such as at an angle of 110° with respect to the cannula 221. In FIG. 22, insertion device 220 is shown with a sinus dilator 100 mounted thereon with the proximal end of the dilator 100 extending into an internal cavity 227 of the retention tip 222. The wings of proximal anchor 107 extend through slots of a slotted flange 229 on the retention tip 222. Insertion device 220 has a flexible rod 225 extending through the cannula 221. The proximal end of rod 225 is connected to the trigger such that moving the trigger in a distal or proximal direction causes the rod 225 to move in a distal or proximal direction, respectively. The distal end of rod 225 has a section 226 with a cross-sectional area that is less than the cross-sectional area of the proximal portion of rod 225, resulting in section 226 having an increased flexibility as compared to the proximal portion of rod 225. The distal end of section 226 abuts against the proximal end of dilator 100 when the dilator is mounted on the retention tip 222 of insertion device 220 (see FIG. 22). Once the dilator 100 is positioned for deployment in a sinus ostium, the user (e.g., physician) moves the trigger in a distal direction, causing the rod 225 and section 226 to also move in a distal direction. As shown in FIG. 23, the distal displacement of the rod 225 and section 226 causes the distal end of section 226 to push the dilator 100 off of the retention tip 222 of the insertion device 220. In certain embodiments, section 226 has sufficient flexibility to bend as the distal end of section 226 encounters the walls of internal cavity 227, eventually pushing the proximal end of dilator 100 out of the internal cavity 227, thus deploying the dilator 100 in a sinus ostium.

Humidity-Regulating Agent

In another aspect, the dilator is osmotically driven. The osmotic dilator is activated and operates by imbibing liquid water from the patient's body through an elastic semipermeable membrane 105 into osmotic tablets 103, 104, which osmotic tablets hydrate and expand radially to mechanically remodel the tissue of the sinus opening 11. The imbibed water can also be in the form of water vapor. Therefore, it is important that the device, prior to use in a patient, be stored and packaged in an environment with sufficiently low moisture to prevent premature imbibition of water in either liquid or vapor form. Conversely, the membrane 105 and osmotic driver 110 require a certain moisture content to activate properly. If either membrane 105 or osmotic tablets 103, 104 are excessively dried during storage, they lose the minimum equilibrium water content necessary for the device to begin expanding in a timely manner after insertion into a patient. In order for the membrane and osmotic engine to function properly, that removed moisture would first need be replaced. In those instances involving a shorter duration of dilation (e.g., 0.5 to 2 hours), such an equilibrium water replacement process leads to an unacceptably and prolonged startup period. Therefore before use, it is important to store the osmotic dilator 100 within a package wherein the environment is neither too dry nor too humid.

Each component of the osmotic driver 110 has associated with it an equilibrium moisture sorption isotherm. For example, in some cases, the osmotic tablet includes polyethylene oxide, which maintains a moisture content of about 5 wt % or less when stored in 65% relative humidity or less. If exposed to about 70% relative humidity or greater, the polymer equilibrates to a higher equilibrium moisture content and swells accordingly. Therefore, an osmotic driver 110 with polyethylene oxide as an osmotic tablet 103, 104 component will imbibe water and swell prematurely in a package if the air within the package has a relative humidity of 70% humidity or greater. Components of elastic semipermeable membrane 105 likewise have equilibrium moisture contents. For example, polyvinyl pyrrolidone grade 12 PF, a hydrophilic polymer added to membranes to make them more permeable to water, absorbs 25 wt % moisture when exposed to relative humidity of 70%. At this relative humidity, the polymer may absorb excessive moisture to the extent that the polymer becomes tacky, which may cause the dilator to stick to the packaging material. By contrast, the same polymer stored in lower relatively humidity such as 50%, may absorb only 18% moisture and thus is substantially less tacky.

In certain embodiments, the osmotic dilator 100 is packaged within a sealed water-impermeable and water vapor-impermeable package. Such packages are typically comprised of a metal foil, or metalized layer in a laminate material. In accordance with some embodiments, the package contains a humidity-regulating agent (e.g., a desiccant) which controls the relative humidity within the package to within the range of about 30 to 50%. This relative humidity range prevents both (i) pre-mature swelling and formation of tackiness, and (ii) excessive lag time during the onset of swelling when dilator 100 is first inserted into a sinus opening of a patient.

In certain embodiments, the humidity-regulating agent is an osmotic salt. Osmotic salts have the properties of maintaining a constant relative humidity when present in a sachet or canister of a desiccant pack stored in a closed space, such as in a product package. These osmotic salts function by establishing an equilibrium exchange of moisture between the water vapor within the headspace of the package and saturated solution on the surface of the osmotic salt which is present in excess as a solid within the desiccant pack. The humidity-regulating agent (e.g., osmotic salt) can be configured to achieve a controlled humidity environment for storage of an osmotic dilator. For example, magnesium chloride maintains a constant relative humidity of about 33 to 31% over a typical storage temperature range of 20 to 37° C. Likewise, potassium carbonate maintains a constant relative humidity of 44 to 41% over a temperature range of 20 to 37° C. Such humidity-regulating agents (e.g., osmotic salts) can be used as desiccants to control and maintain relative humidity within the package of an osmotic dilator 100 to maintain the relative humidity within the desired range.

Aspects of the present disclosure include a kit including a device for dilating a stenotic opening of a paranasal sinus in a subject. The kit includes the device and a sealed package containing the device. The device includes an expandable portion configured to expand from a non-expanded configuration to an expanded configuration. The non-expanded configuration is sized to be positioned within the stenotic opening. The device also includes a self-expanding osmotic driver configured to expand the expandable portion from the non-expanded configuration to the expanded configuration, wherein the expanded configuration dilates the stenotic opening. The sealed package is water impermeable and contains a humidity-regulating agent.

In certain embodiments, the osmotic driver includes a semipermeable membrane that includes a hydrophilic polymer having an equilibrium water content range. The humidity-regulating agent may be configured to maintain the water content of the hydrophilic polymer within the equilibrium water content range. In some instances, the osmotic driver includes an expandable osmotic core that expands upon exposure to water. The humidity-regulating agent may be configured to prevent the osmotic core from expanding while in the sealed package.

In certain embodiments, the humidity-regulating agent is configured to maintain the relative humidity within the sealed package at a relative humidity of from 10% to 90%, such as from 20% to 80%, including from 20% to 70%, or from 20% to 60%, or from 30% to 60%, or from 30% to 50%, or from 30% to 40%. In some cases, the humidity-regulating agent is configured to maintain the relative humidity within the sealed package at a relative humidity of from 30% to 50%.

Sinus Dilator Proximal Anchor

In certain embodiments, the proximal anchor of the sinus dilator is configured to have a size (e.g., length) such that during placement of the device in the maxillary sinus, the proximal end of the device contacts the opposing wall of the nasal cavity facing the sinus ostium. In some instances, the proximal end of the proximal anchor contacts the opposing wall of the nasal cavity facing the sinus ostium. In some cases, the proximal end of the device (e.g., the proximal end of a mounting member at the proximal end of the device) contacts the opposing wall of the nasal cavity facing the sinus ostium. As such, the proximal end of the device may be an elongated proximal end. In some instances, the elongated proximal end prevents the device from being squeezed out of the sinus opening and into the nasal passageway during device expansion of the device. A device configured in such a manner may facilitate a sinus dilator that does not include a distal anchor (e.g., the distal anchor being the anchor positioned inside the sinus cavity). In some instances, the proximal end of the device may not directly contact the opposing wall of the nasal cavity facing the sinus ostium. In these embodiments, a packing material may be positioned between the proximal end of the device and the opposing wall of the nasal cavity such that the device indirectly contacts the opposing wall of the nasal cavity. In some instances, a sinus dilator that does not include a distal anchor may facilitate embodiments where the sinus dilator is inserted into the patient for a short period of time (e.g., 8 hours or less, or 6 hours or less, or 4 hours or less, or 2 hours or less).

In one aspect, a device for dilating a stenotic opening of a maxillary sinus in a subject is provided. In certain embodiments, the device has a self-expanding driver configured to expand an expandable portion from a non-expanded configuration to an expanded configuration. In some cases, the expandable portion is disposed peripherally around the driver and configured to expand from the non-expanded configuration to the expanded configuration, where the non-expanded configuration is sized to be positioned within the stenotic opening. In certain instances, the device also has a proximal anchor proximate to the proximal end of the device, the proximal anchor being sized and configured to prevent the device from passing through the stenotic opening into the maxillary sinus cavity.

Figure 18:
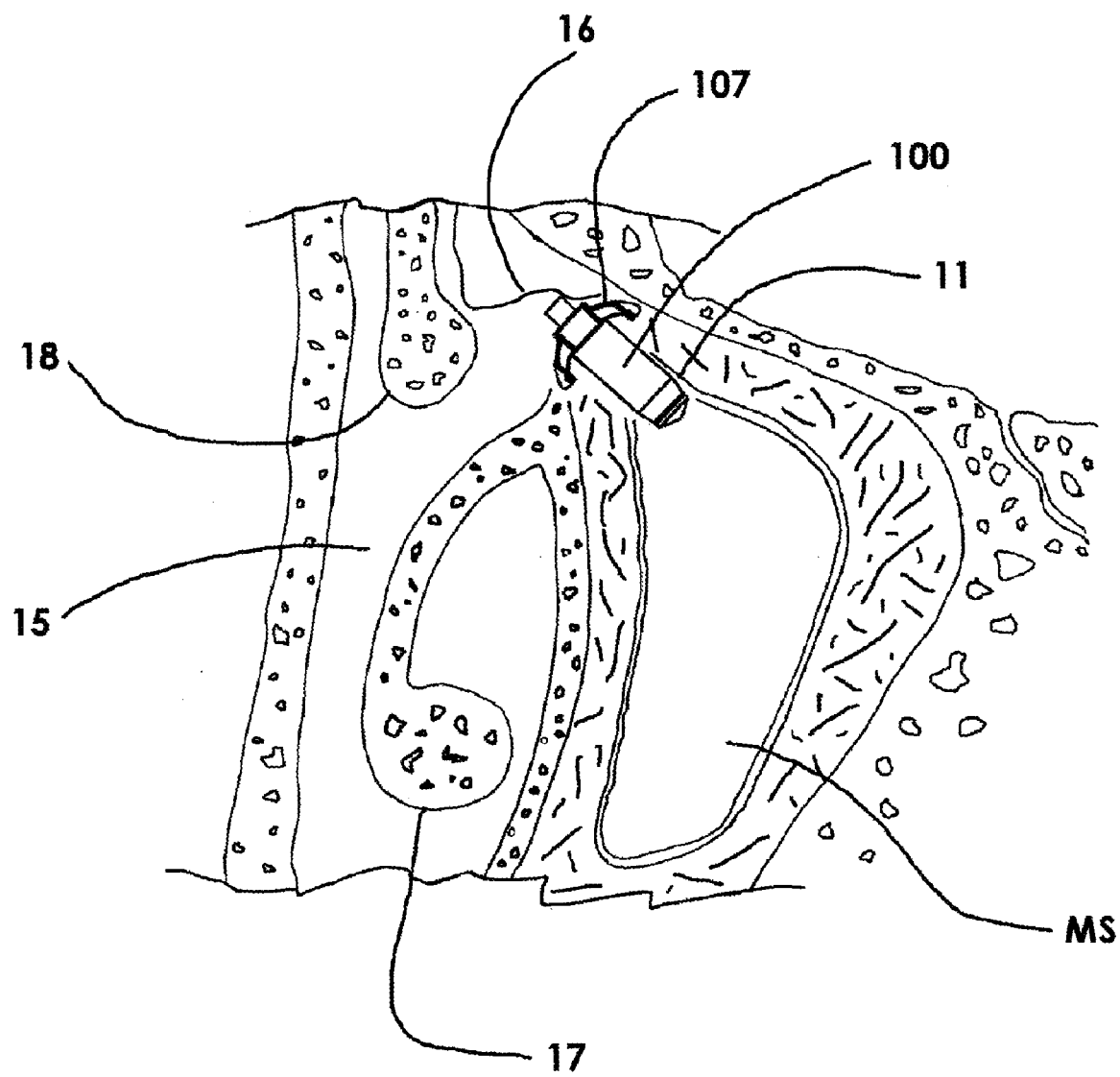
FIG. 18 is a side view of the dilation device shown in FIG. 17 after being inserted into a maxillary sinus opening.

In some cases, the device has an elongated proximal end with a length such that at least a portion of the proximal end of the device contacts a wall of the nasal cavity facing the stenotic maxillary sinus opening. In certain embodiments, the proximal end of the device is sized to fit between the sinus opening and the opposing wall of the nasal cavity (e.g., the nasal passageway). As such, in some cases, the device has a length, measured from a point on the device that is immediately adjacent to the nasal passageway side of the sinus opening, to the proximal end of the device, which approximates the distance between the sinus opening and the opposing wall of the nasal cavity in a subject. For example, the length of that portion of the device which extends from the nasal passageway side of the sinus opening to the opposing wall of the nasal cavity of a subject, may have a length d (see FIG. 5), measured from a point on the device that is immediately adjacent to the nasal passageway side of the sinus opening, to the proximal end of the device, of 1 to 10 mm, such as 2 to 7 mm, including 3 to 6 mm, or 3 to 5 mm. In certain cases, the device has a length, measured from a point on the device that is immediately adjacent to the nasal passageway side of the sinus opening, to the proximal end of the device, of 3 to 6 mm. In some instances, the elongated proximal end of the device forms at least a portion of the proximal anchor and when wedged against the opposing wall of the nasal cavity keeps the expanding device from being squeezed out of the sinus opening and into the nasal cavity as shown in FIG. 18.

In certain embodiments, the proximal anchor includes a member extending radially outward from an axis (e.g., a longitudinal axis) of the device. The member may be configured to anchor the device in the stenotic opening and to prevent the device from entering further into the sinus cavity of the subject. In some cases, the member of the proximal anchor prevents the device from entering entirely into the sinus cavity of the subject, thus positioning the device within the stenotic opening of the subject during use.

In some instances, the proximal anchor includes one or more members as described above, such as 2 members, 3 members, 4 members, 5 members, 6 members, 7 members, 8 members, 9 members, or 10 members. In certain cases, the proximal anchor includes a pair (e.g., 2) of the radially outward extending members. In embodiments, where the proximal anchor includes 2 radially outward extending members, the members may be positioned on opposite sides of the axis (e.g., longitudinal axis) of the device.

In certain instances, each of the members extends radially outward from the axis of the device a distance of 1 mm or more, such as 2 mm or more, including 3 mm or more, or 4 mm or more, or 5 mm or more, or 6 mm or more, or 7 mm or more, or 8 mm or more, or 9 mm or more, or 10 mm or more. In some cases, each of the members extends radially outward from the axis of the device a distance of 3 mm or more. In certain embodiments, each of the members extends radially outward from the axis of the device a distance of 1 to 10 mm, such as 2 to 9 mm, including 4 to 8 mm, or 5 to 7 mm. In some instances, each of the members extends radially outward from the axis of the device a distance of 4 to 8 mm.

Sinus Dilator Cone-Shaped Distal Tip

In certain embodiments, the sinus dilator includes a distal tip. The distal tip may be configured to facilitate inserting the sinus dilator into a stenotic opening (e.g., a setnotic sinus ostium). For example, the distal tip of the sinus dilator may have a shape that facilitates insertion into a stenotic opening. In certain instances, the distal tip has a tapered shape. By tapered is meant that the cross-sectional area of the distal tip decreases from the proximal end of the distal tip to the distal end of the distal tip, such that the cross-sectional area of the distal end of the distal tip is less than the cross-sectional area of the proximal end of the distal tip. Various tapered shapes may be used for the distal tip, such as, but not limited to, a cone-shape, a pyramid shape, a frustum shape, and the like. In some instances, the distal tip has a cone-shape.

In certain instances, the cone-shaped tip has an apex angle of 10° to 80°, or 20° to 70°, or 30° to 70°, including 40° to 70°, such as 50° to 70°. In certain cases, the cone-shaped tip has an apex angle of 60°.

In certain embodiments, the distal tip includes a proximal surface in contact with the driver of the sinus dilator. The proximal surface of the distal tip may be configured to direct expansion of the driver radially outwardly from an axis (e.g., the longitudinal axis) of the sinus dilator, rather than in a direction that is parallel to the longitudinal axis of sinus dilator.

In certain instances, the tip is made from a material that is substantially rigid, such that it can direct expansion of the driver radially outwardly from an axis (e.g., the longitudinal axis) of the sinus dilator without substantially changing shape (e.g., bending). In some cases, the tip is made from a material, such as, but not limited to, metal, plastic, ceramic, combinations thereof, and the like.

In certain embodiments, sinus dilator has a passageway (e.g., a central passageway or conduit) extending through at least a distal end of the sinus dilator. In these embodiments, the tip may include a post extending proximally from the proximal face of the tip. The proximally extending post may be configured to engage the passageway. For example, the proximally extending post may be configured to be inserted into the passageway. Insertion of the proximally extending post into the passageway of the sinus dilator may facilitate attachment of the tip to the sinus dilator.

Figure 3:
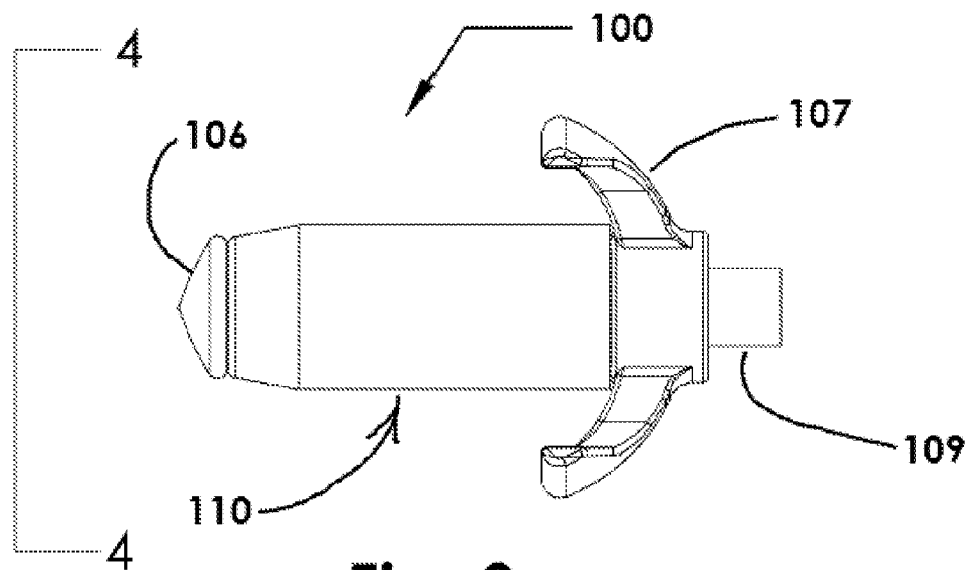
FIG. 3 is a side view of an osmotically driven device for dilating a paranasal sinus opening, in a non-expanded configuration, according to embodiments of the present disclosure.

One embodiment of an osmotic dilator 100 which illustrates several aspects of the present disclosure is shown in a side view in FIG. 3, in end view in FIG. 4, and in a sectional view in FIG. 5. The dilator 100 includes an osmotic driver 110, a tapered distal tip 106, a proximal anchor 107 and a mounting member 109. Dilator 100 is shown in a non-expanded configuration in FIGS. 3 to 5. Dilator 100 includes tube 101 (e.g., a non-collapsible metal or plastic tube) having the osmotic driver 110 disposed thereon. As best shown in FIG. 5, the driver 110 is comprised of an inner membrane 102 disposed on the tube 101, two osmotic tablets 103, 104 threaded over the membrane 102 and tube 101 and an elastic semipermeable membrane 105 applied thereover. In use, the dilator 100 is placed in the sinus opening of a living subject, typically a human subject. Water from the subject's body and tissues permeates through the elastic semipermeable membrane 105 due to the presence of an osmotic pressure difference caused by the osmotically active agent(s) contained in tablets 103 and 104. As water permeates into the tablets 103, 104, they begin to swell. Since tube 101 is made of an incompressible material (e.g., stainless steel) and since anchor 107 and tip 106 are also made from relatively incompressible materials (e.g., plastic, metal or ceramic), the swelling of tablets 103, 104 causes the device 100 to expand in a radially outward direction. In other words, the diameter of osmotic driver 110 increases. The swelling tablets 103, 104 cause the elastic membrane 105 to expand to accommodate the increasing volume of the tablets 103, 104. As disclosed in greater detail in U.S. patent application Ser. No. 13/219,505, filed Aug. 26, 2011, the disclosure of which is incorporated herein by reference, the expanding osmotic driver 110 exerts pressure on the surrounding tissue and bone of the sinus opening, causing the opening to permanently dilate. By controlling membrane thickness and composition, the period for complete expansion of the driver 110 is at least 0.5 hours. Expansion over a period of at least 0.5 hours is desirable since it avoids patient discomfort and tissue damage experienced with abrupt short-term dilation times as are encountered in balloon sinuplasty procedures. In those applications where the dilation procedure using the dilators disclosed herein occurs in a physician's office setting while the subject is awake and waiting, dilation typically occurs over a period of less than 2 hours, though longer dilation times may optionally be used.

In accordance with one aspect, the dilator 100 includes a tapered distal tip 106 that can be formed of plastic, metal or ceramic. Tip 106 may be secured to the tube 101, e.g., by gluing post 108 into the central lumen of tube 101 or by creating a mechanical (e.g., screw threads) or friction connection between tube 101 and post 108. As shown in FIG. 5, the distal surface of tip 106 is tapered at an angle α relative to the axis of the device, which provides a conical shape to the distal side of the tip 106. The tapered tip 106 makes it easier for the physician to insert the dilator 100 into the closed or partially closed sinus ostium. In certain embodiments, the angle α ranges from 20° to 70°. In other embodiments, the angle α ranges from 50° to 70°. In other embodiments, the angle α is 60°.

Figure 6:
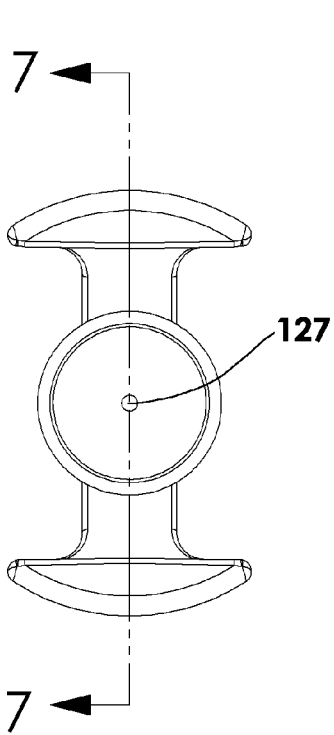
FIG. 6 is an end view of an osmotically driven device for dilating a paranasal sinus opening, in a non-expanded configuration, according to embodiments of the present disclosure.

FIGS. 6 and 7 show an alternate embodiment of the osmotic dilator 100 shown in FIGS. 3 to 5. In this embodiment, dilator 120 has a tapered distal tip 126. Like distal tip 106 of dilator 100, distal tip 126 also has a conical shape and the angle α ranges mentioned above for tip 106. Unlike tip 106, tip 126 has a passageway (e.g., a conduit) 127 that is in fluid communication with the central lumen of tube 121. Thus when dilator 120 is inserted into the sinus ostium, the passageway 127 and tube 121 allow gas and fluid to be introduced into the paranasal sinus cavity, or to come out of the paranasal sinus cavity. Thus bodily fluids such as mucous and blood can be drained out of the sinus cavity through passageway 127. Likewise fluids such as a drug solution, saline, etc. can be introduced into the sinus cavity via the lumen of tube 121 and passageway 127. The conical tip 126 can be slipped over tube 101 and secured to the outside of tube 101 with adhesive. Alternatively, the interior surface of passageway 127 can be formed with screw threads and tube 101 can be formed with matching threads in order to secure the tip 126 to tube 101. Once screwed on, the tip 126 in this configuration can be further bonded with a small amount of adhesive. In yet another configuration, the conical tip 126 with passageway 127 can be slipped onto tube 101 which tube end is then formed with a slight flare where the diameter of the flare is greater than the diameter of passageway 127.

Although FIGS. 3 through 7 show conical tips 106, 126 having a relatively flat angled outer surface, those skilled in the art will appreciate that the outer surface of tips 106, 126 can also be curved or rounded, e.g., to form a bullet-shaped distal end, as long as the surfaces approximate the angle α ranges specified above for flat outer surfaces. Thus, the terms "conical" and "cone-shaped" when referring to tips 106, 126 refer to both flat and curved outer distal surfaces.

In accordance with another aspect, the device 100 includes a proximal anchor 107 positioned adjacent the proximal end thereof. Anchor 107 may be secured (e.g., by gluing) to the tube 101. As best shown in FIG. 4, the proximal anchor 107 has two projecting members 111, 112 that extend radially outward from the central axis of the dilator 100 a sufficient distance and having sufficient stiffness, that the anchor 107 cannot be easily pushed through the sinus ostium during dilator 100 placement. For a device used to dilate a maxillary sinus, the projecting members each typically extend out a distance of at least about 3 mm from the axis of the device 100. In other embodiments the projecting members each typically extend out a distance of about 4 to 8 mm from the axis of the device 100. The total extension of the two projecting members 111, 112 should be greater than the maximum diameter achieved by the osmotic driver 110. Thus, for a driver 110 having a maximum expanded diameter of 5 mm, each of the projecting members extend out at least 3.5 mm from the central axis of the device 100. In this way, the anchor 107 prevents the device 100 from being squeezed out of the maxillary sinus opening 11 and into the cavity of the maxillary sinus (MS) during device expansion. In certain embodiments, the anchor 107 can include only a single projecting member 111 or 112.

Figure 17:
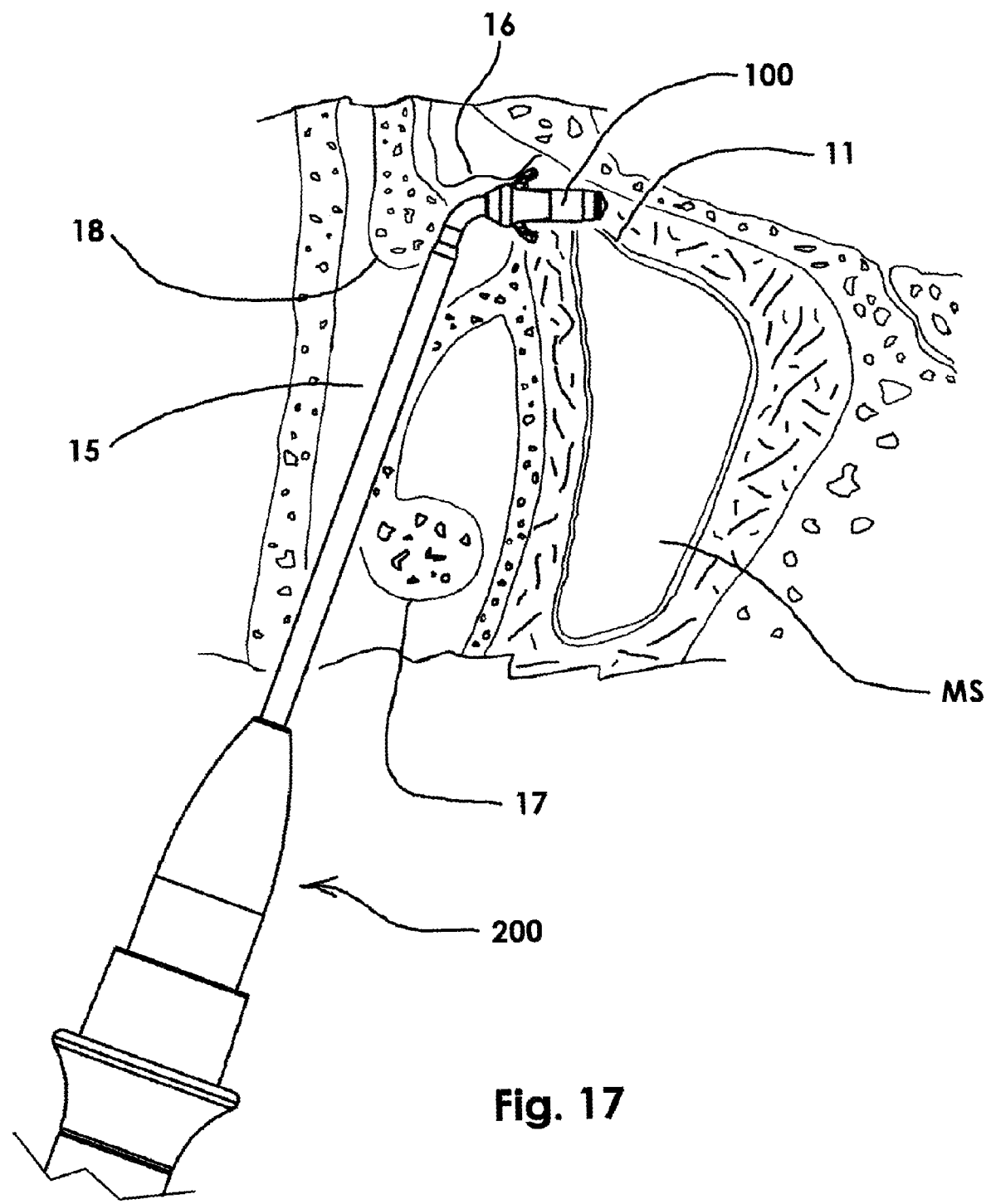
FIG. 17 is a side view of an insertion device and a dilation device used to insert the dilation device into the opening of a maxillary sinus which is shown in section, according to embodiments of the present disclosure.

As best shown in FIG. 4, the projecting members 111 and 112 extend out from opposite "sides" of device 100 which gives the anchor 107 a more 2-dimensional configuration than if the projecting members extended out from the entire circumference of device 100. As shown in FIGS. 17 and 18, such a 2-dimensional configuration is helpful to navigate device 100 through a subject's nostril and past bony turbinates 17 and 18 located in nasal passageway 15 en route to placing device 100 in the maxillary sinus opening 11.

Referring now to FIGS. 5 and 7, in cases where the dilator 100 is to be used to dilate the maxillary sinus ostium, the distance d between the distal ends of the projecting members 111, 112 and the proximal end of the dilator 100 (or 120) should be sufficient to allow the proximal end of the dilator to engage a wall 16 of the nasal passageway 15 which faces the maxillary sinus opening 11. That is to say that the proximal end of the dilator engages or abuts against the wall 16 when the expanding portions of the dilator 100 (or 120) are positioned within the maxillary sinus opening 11. In certain embodiments, distance d ranges from about 3 to 6 mm for a dilator 100 that is adapted to dilate the maxillary sinus opening 11 of an adult human. In other embodiments, the distance d ranges from 4 to 5 mm. As best shown in FIG. 18, when dilator 100 (or 120) is positioned within opening 11, the proximal end of dilator 100 abuts against wall 16. This abutment keeps dilator 100 from being squeezed out of the opening 11 and into the passageway 15 as dilator 100 expands. Similarly, the projecting members 111 and 112 of proximal anchor 107 prevent the dilator 100 from being squeezed into the maxillary sinus cavity (MS) as dilator 100 expands.

The proximal anchor 107 and mounting member 109 can be a single integrated item, or separate items as shown in FIG. 5. When formed as separate items, mounting member 109 can be attached to tube 101 using adhesive and/or provided with internal threads that screw onto matching threads on the external surface of tube 101. The threaded mounting member 109 can be further secured with a small amount of adhesive. Alternatively, member 109 can be slipped over tube 101 which tube is mechanically flared on the end such that the outside diameter of the flare is greater than the inside diameter of member 109. One advantage of having mounting member 109 in a two-part assembly is that proximal anchor 107 can be composed of a soft, flexible material suitable to conform with live tissue structures while the mounting member 109 can be made of a hard material which provides a more secure adhesive or mechanical connection to tube 101. Together anchor 109, the proximal end portion of tube 101 and member 109 provide anchoring which keeps the device 100 locked in the sinus opening during device 100 expansion and prevents the device 100 from being squeezed out of the sinus opening in either direction; the projecting members 111 and 112 prevent the device 100 from being squeezed into the maxillary sinus cavity (MS), while the member 109 and the proximal portion of tube 101 prevent the device 100 from being squeezed into the nasal cavity. In certain embodiments, this anchoring configuration is simpler than a dual anchor design (e.g., a device with both a proximal and distal anchor), since there is no need to have a distal anchor which must be initially pushed through the stenotic sinus opening. The single anchor with bi-directional anchoring functionality is particularly useful for short term dilations (e.g., dilation times of up to about 2 hours duration), e.g., where the patient never leaves the doctor's office while the device 100 is in use.

Figure 8:
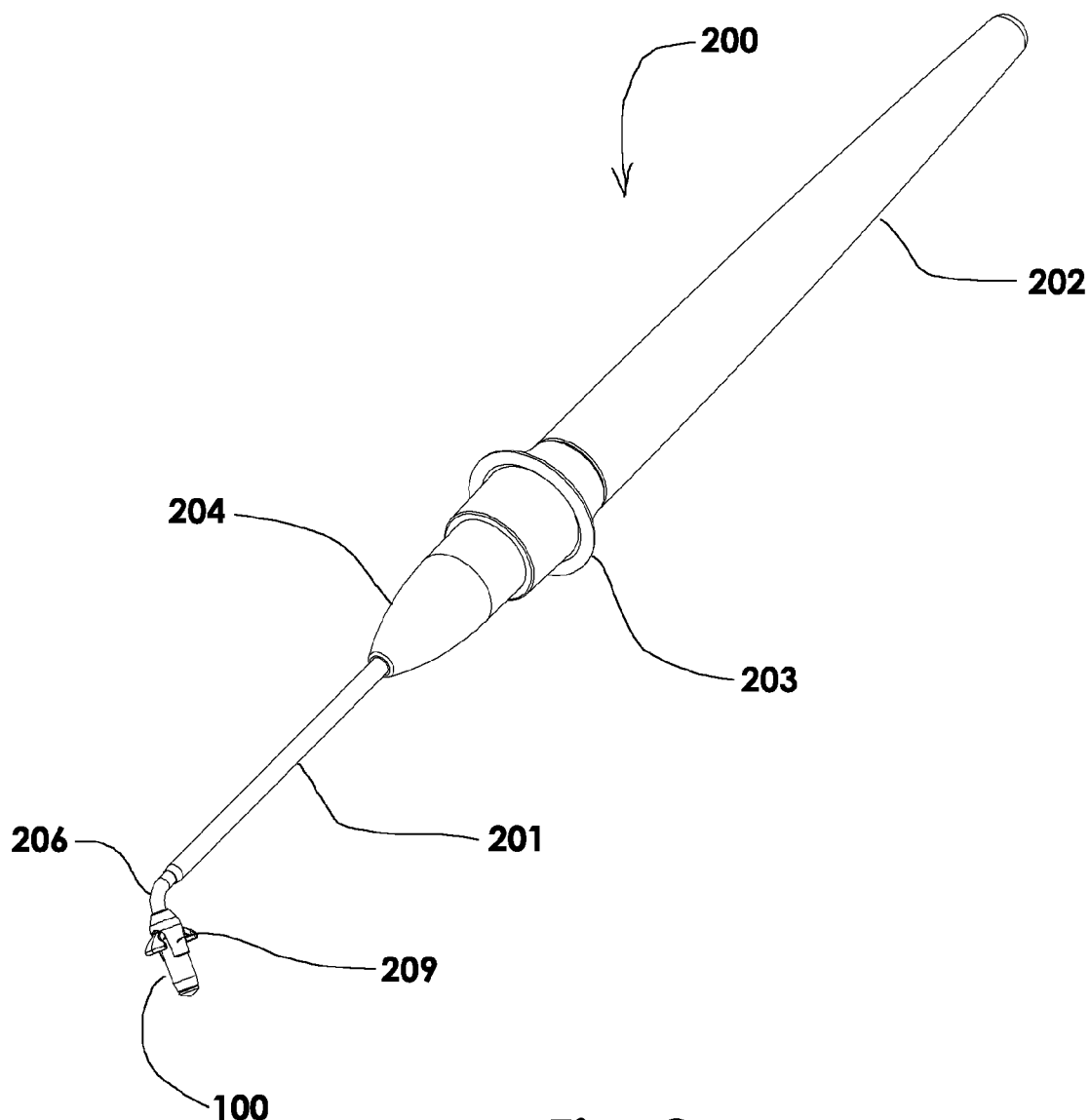
FIG. 8 is a perspective view of an insertion device for inserting a dilation device, according to embodiments of the present disclosure.
Figure 10:
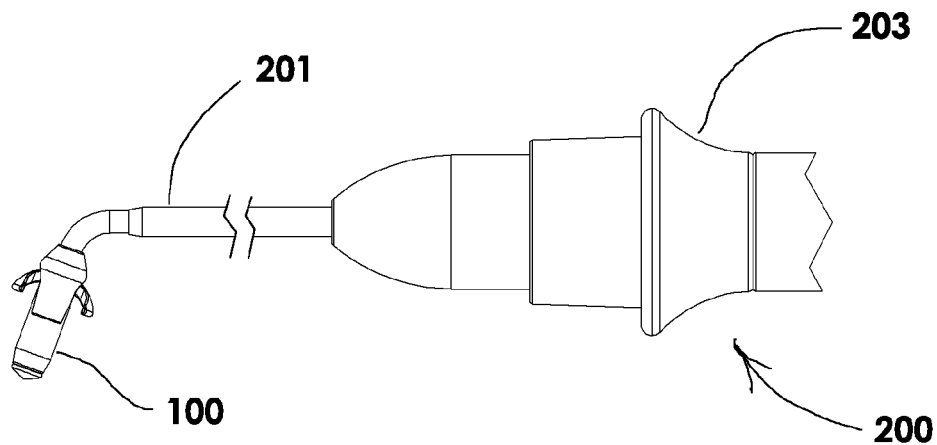
FIG. 10 is a side view of the devices shown in FIG. 8.
Figure 11:
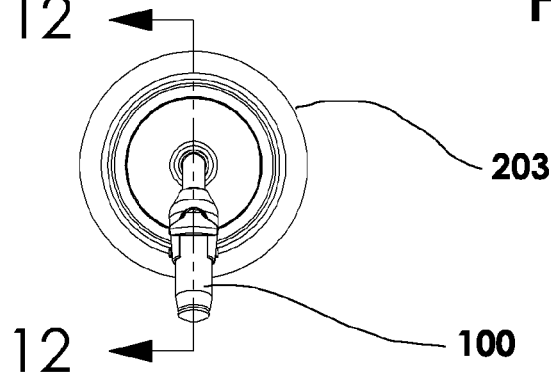
FIG. 11 is an end view of the device shown in FIG. 10.
Figure 12:
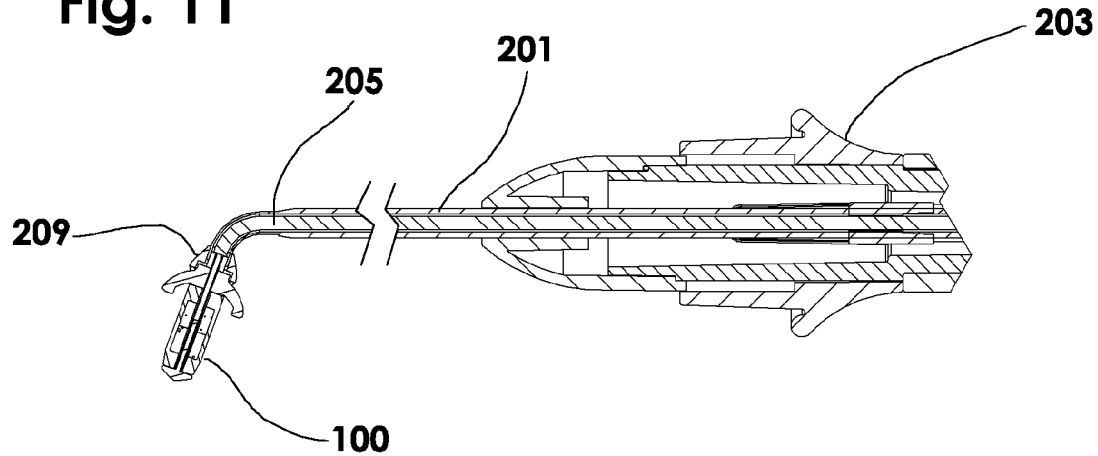
FIG. 12 is a sectional view of the devices shown in FIG. 11, taken along line 12-12.
Figure 13:
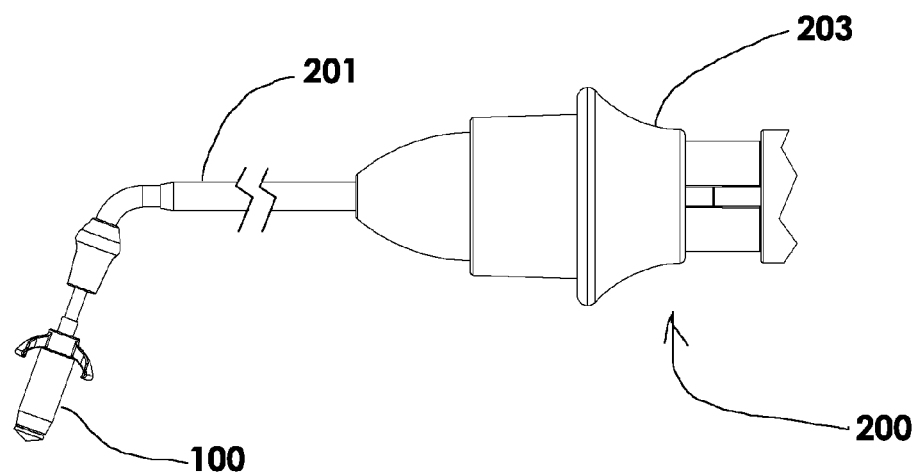
FIG. 13 is a side view of the devices shown in FIGS. 10 to 12, with a trigger activated to displace the dilation device, according to embodiments of the present disclosure.
Figure 14:
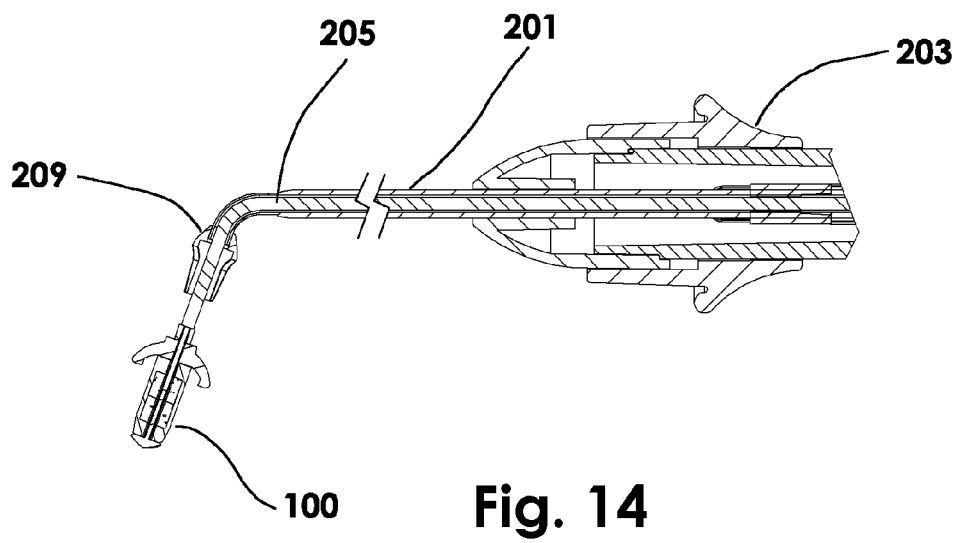
FIG. 14 is a sectional view of the devices shown in FIG. 13.
Figure 15:
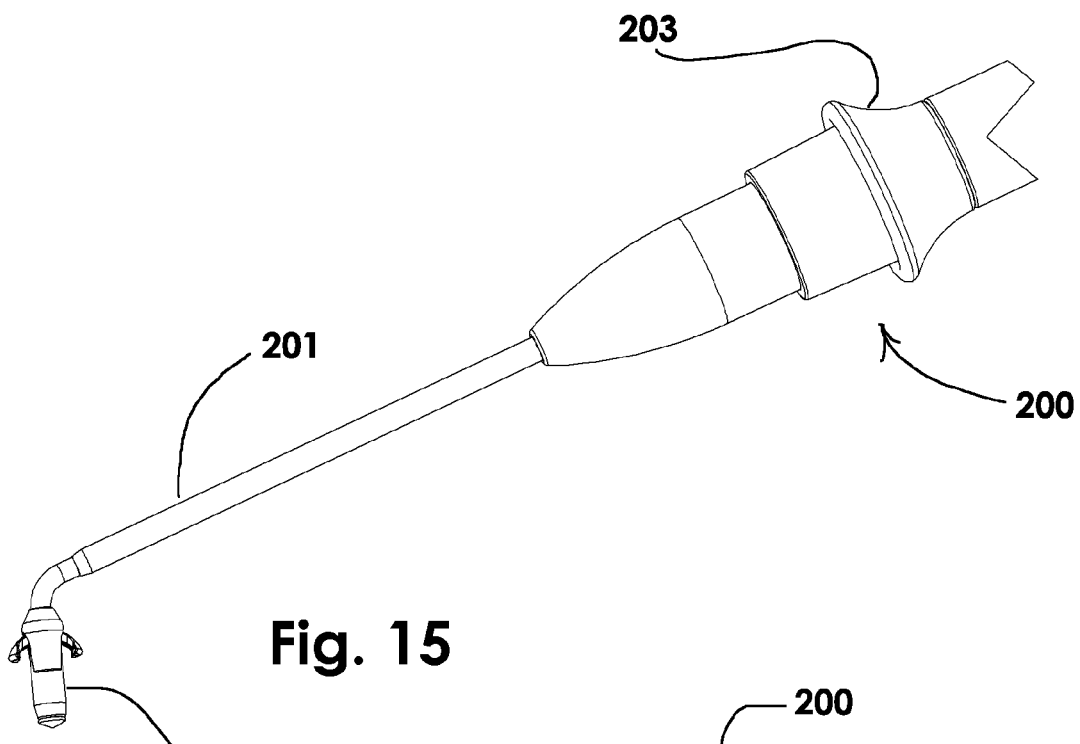
FIG. 15 is a perspective view of the devices shown in FIG. 13.
Figure 16:
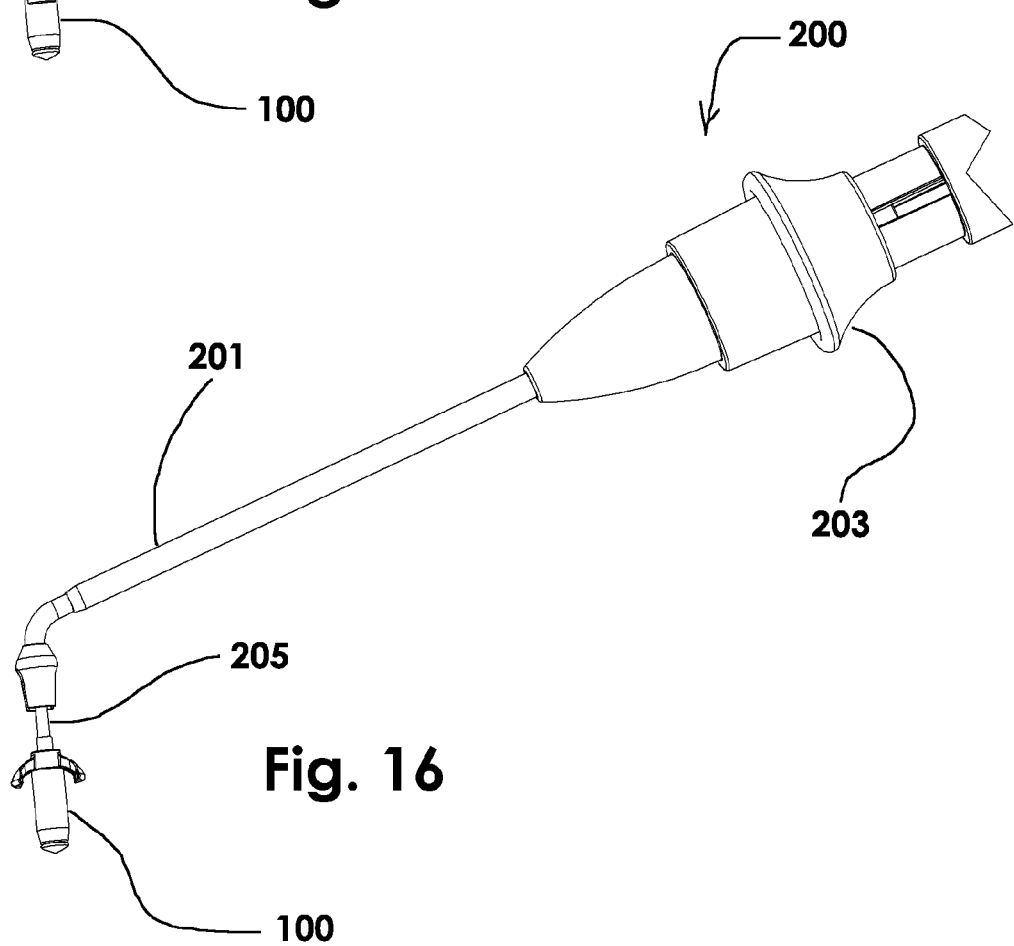
FIG. 16 is a perspective view of the devices shown in FIG. 14.

The insertion of a dilator 100 into a stenotic paranasal sinus opening is as follows. A maxillary sinus opening is used for the purpose of illustration. Referring first to FIG. 8, there is shown one embodiment of a sinus ostium dilator insertion device 200. Device 200 has a handle 202, a cannula 201 mounted on the distal end 204 of handle 202, the handle 202 having a slidable trigger 203. The distal end of cannula 201 has a bend 206 and a slotted flange 209 upon which dilator 100 is mounted. The slots in flange 209 are sized to slidably engage the projecting members 111 and 112 of proximal anchor 107 such that the projecting members 111 and 112 extend out of the slots of flange 209 and prevent axial rotation of the dilator 100 during insertion into a stenotic sinus opening (see also FIGS. 3-5). Referring now to FIGS. 10 to 12, with dilator 100 mounted onto the distal end of device 200, the sliding trigger 203 is in its proximal position. The trigger 203 is connected to flexible rod 205 via conventional means and at least one slot in handle 202 (the connection is not shown in the figures). Rod 205 is slidably positioned within cannula 201. The rod 205 can be for example made from metal or plastic and has a diameter just slightly less than the inner diameter of cannula 201. The proximal end of rod 205 is operatively connected to trigger 203 by conventional means. With the sliding trigger 203 oriented in the proximal position (e.g., the right position as shown in FIGS. 10 and 12), the dilator 100 is mounted on the distal end of insertion device 200 and is ready for deployment into a sinus opening. In this position, the rod 205 is recessed a sufficient distance from the distal end of cannula 201 to accommodate mounting member 109 to fit within the interior lumen of cannula 201.

In use, and as best shown in FIGS. 17 and 18 using the maxillary sinus (MS) for purposes of illustration, the mounted dilator 100, and cannula 201 are advanced through the subject's nostril and then through the nasal passageway 15, until the distal tip of dilator 100 abuts against the stenotic opening 11. Then the physician applies further force on handle 202 and pushes the dilator 100 into the sinus opening 11 until the projecting members 111 and 112 of proximal anchor 107 abuts against the tissue surrounding the nasal passageway side of opening 11. Because the proximal anchor 107 abuts against the ends of the slots in flange 209, the dilator 100 can be pushed into a narrowed, stenotic and/or completely closed opening 11 by the physician applying a distally oriented pushing force via the handle 202. Once in position within the opening 11, the physician may slide the trigger 203 to the distal position (e.g., the left position as shown in FIGS. 13, 14, 15 and 16), and the rod 205 is advanced out of the interior lumen of cannula 201 which causes the dilator 100 to be pushed off the distal end of device 200. Following, the insertion device 200 is withdrawn from the patient. As mentioned earlier and as shown in FIG. 18, the inserted dilator 100 has the proximal end of mounting member 109 abutting against the tissue of wall 16 (see also FIG. 17) facing the sinus opening 11. Likewise the projecting members 111 and 112 of proximal anchor 107 abut against the tissue surrounding the nasal passageway side of opening 11. In this way, the dilator 100 is substantially anchored in place during its expansion phase and will not be squeezed out of the opening 11 during the expansion.

In certain embodiments, device 200 includes a light source (not shown in the figures), which in some instances is a directional light source, such as a fiber optic light source, a laser (e.g., a low energy laser), and the like. The light source emits light into the lumen of cannula 201 using known light directing means and a light-reflecting interior surface of cannula 201. In some embodiments, rod 205 and dilator 100 (or 120) are also constructed of light transmitting and/or translucent materials so that the light from the light source causes at least portions of the dilator 100 (or 120) to become illuminated. The illumination may have sufficient intensity so that the emitted light can be seen through the patient's facial tissue. The position of the illuminated dilator 100 (or 120) may help the physician to correctly position the dilator in the ostium of a paranasal sinus. Alternatively, the dilator 120 described herein may be placed using an illuminated guide wire that extends through the cannula 201 and/or through rod 205 and optionally through the internal lumen of tube 121 and passageway 127 of dilator 120.

Other suitable dilator insertion devices are disclosed in FIGS. 3-12, 18-20 and 24 of U.S. patent application Ser. No. 13/219,497 filed Aug. 26, 2011, the disclosure of which is incorporated herein by reference.

Sinus Dilators Configured for Drug Delivery

In certain embodiments, the device (e.g., sinus dilator) includes one or more drug reservoirs configured to deliver a drug to the subject while the device is positioned within the stenotic opening. The drug reservoir may be configured to deliver the drug locally to the tissues surrounding the device while the device is in use. For example, the drug reservoir may be configured to deliver the drug to one or more of the interior tissues of the stenotic opening, the interior lumen of the paranasal sinus, the tissues of the stenotic opening, the exterior tissues of the stenotic opening, and the nasal cavity.

The one or more drug reservoirs may have a variety of different configurations. For example, embodiments of the sinus dilator may include two drivers as described above (e.g., a proximal driver and a distal driver). In these embodiments, the drug reservoir may be positioned between the first and second drivers. In these instances, positioning of the drug reservoir between the first and second drivers may facilitate delivery of the drug to one or more of the interior tissues of the stenotic opening, the interior lumen of the paranasal sinus, and the like. For instance, in certain embodiments, the device may be configured to deliver the drug from the drug reservoir through the action of the first and second drivers. In embodiments where the drivers include a swellable polymer or an osmotically active agent, expansion of the drivers may apply external pressure on the sides of the drug reservoir contacting the first and second drivers and push the drug out of the drug reservoir. For example, expansion of the first and second drivers may compress the drug reservoir and thus force the drug out of the drug reservoir. As such, in certain embodiments, the drug reservoir is configured to release a drug as the first and second drivers (e.g., first and second osmotic drivers) expand from a non-expanded configuration to an expanded configuration. In these embodiments, the expandable portion of the sinus dilator may include an elastic semipermeable membrane. The expandable portion may surround the drivers of the sinus dilator, such that the drivers are within the periphery of the expandable portion. As such, in certain embodiments, the device includes a drug reservoir positioned between the first and second drivers and within the periphery of the expandable portion. An elastic semipermeable membrane may facilitate drug delivery from the device as the drug diffuses through the membrane during use of the device. In some cases, the portion of the membrane overlying the drug reservoir may include one or more orifices through which drug released from the drug reservoir can pass through to be released to the surrounding environment.

In other embodiments, the sinus dilator includes a drug, where the drug is the osmotically active agent in the driver of the sinus dilator. In some instances, the osmotically active agent is a drug (e.g., an osmotically active drug agent). In these embodiments, the driver of the sinus dilator may be configured to expand osmotically as described herein, as well as release the drug from the device into the surround tissues. In some instances, including an osmotically active agent that is a drug may facilitate a simplification of the device as the osmotically active agent acts both as the osmotically active agent for the driver and is the drug (e.g., the pharmacologically active agent) that may be released from the device during use. In some embodiments, the expandable portion of the sinus dilator may include an elastic semipermeable membrane. An elastic semipermeable membrane may facilitate drug delivery from the device as the drug diffuses through the membrane during use of the device.

In certain embodiments, as discussed above, the driver includes an osmotically active drug agent. The driver may also include other components in the driver composition, such as, but not limited to, a solvent, a diluent, a lubricant, an excipient, combinations thereof, and the like. In some cases, the driver may also include a non-drug osmotically active agent as described herein. In some instances, the driver includes a vehicle, such as a liquid vehicle for carrying the osmotically active drug agent. For example, the osmotically active drug agent may be present in a liquid vehicle as a finely-divided dispersion or as a solution. The vehicle may be comprised of one or more of the following: aqueous media including water; water with surfactant; water-in-oil emulsion; oil-in-water emulsion; non-aqueous media; ethanol; butanol; polyethylene glycol; poloxamer; glycerin; caprylocaproyl polyoxyl-8 glycerides; diethylene glycol monoethyl ether; glyceryl distearate; polysorbates such as polysorbate 20, 60, or 80; triacetin; benzyl alcohol; castor oil polyoxyl; castor oil polyoxyl hydrogenated; nut oils such as peanut oil; seed oils such as cottonseed, sesame oil, etc.; bean oil such as soy bean oil; a paste such as polyoxyl 15 hydroxystearate, caprylic glycderides, etc.; hydrogenated coco-glycerides; short chain partial glycerides such as gylceryl mono-, di- and tri-hexanoate; caprylic/capric glycerides; glycerol monooleate; glycerol ricinoleate; mixtures of the above; and the like.

In certain embodiments, the drug is water soluble. In some instances, the drug is an antibiotic, an anti-inflammatory drug, a local anesthetic, an analgesic, or a combination thereof. For example, the drug may be selected from antibiotics, anti-inflammatory drugs, anesthetics (e.g., local anesthetics), analgesics (e.g., locally acting analgesics), drugs that reduce bleeding (e.g., vasoconstrictors), combinations thereof, and the like. In certain embodiments, antibiotics include levofloxacin, moxifloxacin, amoxicillin, clavulanic acid, clarithromycin, azithromycin, cefuroxime, ciprofloxacin, salts thereof and combinations thereof and the like. In some instances, anti-inflammatory drugs include methylprednisolone, dexamethasone, salts thereof and combinations thereof and the like. In some cases, local anesthetics include lidocaine, bupivacaine, ropivacaine, tetracaine, salts thereof and combinations thereof and the like. In certain embodiments, locally acting analgesics include: acetaminophen; Cox-2 inhibitors, such as celecoxib and rofecoxib and the like; NSAIDS such as diclofenac, ibuprofen, ketoprofen, naproxen, piroxicam, aspirin and the like; opioids such as morphine; opioid agonists such as tramadol and the like. In certain embodiments, vasoconstrictors include oxymetazoline, epinephrine, tranexamic acid, salts thereof, combinations thereof, and the like. In certain instances, the drug reservoirs may include a combination of drugs, such as a combination of an NSAID, an anti-inflammatory drug and a vasoconstrictor. For example, the drug may include OMS103HP (Omeros Corp., Seattle, Wash.), which includes an NSAID (ketoprofen), an anti-inflammatory drug (amitriptyline) and a vasoconstrictor (oxymetazoline).

In some instances, the drug includes one or more of a corticosteroid (such as, but not limited to, triamcinolone, fluticasone propionate, etc.), glucocorticosteroid (such as, but not limited to, mometasone furoate, budesonide, beclomethasone dipropionate, ciclesonide, etc.), a beta-2-angonist (such as, but not limited to, formoterol fumarate, etc.), combinations thereof, and the like.

Tablet Compression Force

Aspects of the present disclosure include a method of making a device for dilating a stenotic opening of a paranasal sinus in a subject. The method includes forming an osmotic driver in the form of a tablet and an expandable membrane disposed peripherally therearound. The tablet is comprised of an osmotically active agent and an osmopolymer. The driver is configured to expand from a non-expanded configuration to an expanded configuration. The non-expanded configuration is sized to be positioned within the stenotic opening. The method includes compressing the tablet such that the tablet is formed having a smooth outer surface with no flashing. By "flashing" is meant excess material attached to a molded, forged, or cast product, which is usually removed. Flashing is typically caused by leakage of the material between the two surfaces of a mold (beginning along the parting line between the two halves of the mold) or between the base substrate and the mold. In some instances, forming a tablet with substantially no flashing (e.g., with substantially smooth outer surfaces) simplifies the method of manufacturing since excess flashing need not be removed from the compressed tablets before using the compressed tablets in the sinus dilator. In certain instances, forming a tablet with substantially no flashing (e.g., with substantially smooth outer surfaces) facilitates the manufacture of the sinus dilator by minimizing damage to the elastic semipermeable membrane surrounding the osmotic tablet of the sinus dilator.

In certain embodiments, the method includes compressing the osmotically active agent and the osmopolymer in a tablet press. In order to form the tablet with substantially no flashing, the tablet may be compressed with a force less than that which would produce excess flashing. For example, in some cases, the method includes compressing the tablet using a compression force of 200 lbs or less, such as 150 lbs or less, including 100 lbs or less, or 90 lbs or less, or 80 lbs or less, or 70 lbs or less, or 60 lbs or less, or 50 lbs or less, or 40 lbs or less, or 30 lbs or less, or 20 lbs or less, or 10 lbs or less. In certain cases, the method includes compressing the tablet using a compression force of 100 lbs or less. In certain instances, the method includes compressing the tablet using a compression force of 10 lbs to 200 lbs, such as 10 lbs to 150 lbs, including 10 lbs to 100 lbs, or 20 lbs to 90 lbs, or 20 lbs to 80 lbs or 20 lbs to 70 lbs, or 20 lbs to 60 lbs, or 20 lbs to 50 lbs.

In certain cases, the method includes compressing the tablet using a compression force of 20 lbs to 70 lbs. In certain instances, the method includes compressing the tablet using a compression pressure of 5 to 150 mPa, such as 5 to 100 mPa, including 5 to 90 mPa, or 10 to 80 mPa, or 10 to 70 mPa, or 15 to 65 mPa, or 20 to 65 mPa, or 25 to 65 mPa, or 30 to 65 mPa, or 30 to 60 mPa, or 30 to 55 mPa, or 30 to 50 mPa. In some cases, the method includes compressing the tablet using a compression pressure of 15 to 65 mPa. For example, the method may include compressing the tablet using a compression pressure of 30 to 150 mPa.

In some cases, the compression force is still sufficient to produce a tablet that has sufficient cohesiveness such that the tablet remains in substantially one piece after compression and does not break, chip, disintegrate, etc. upon handling of the tablet during the manufacturing and use of the sinus dilator.

In accordance with certain aspects, the osmotic salt tablets 103, 104 are formed by compression molding the tablets using only about 20 to 70 lbs force (see e.g., FIG. 5). The annular shaped tablets 103, 104 can be formed by compressing a tablet granulation composition in a tablet press using flat-faced beveled round tooling having an outside diameter of 2.7 mm and an inside diameter of 0.92 mm. The lower compression force results in less flashing of tablet granulation material during compressing which results in smoother tablet surfaces substantially devoid of rough edges. Smoother tablet surfaces result in fewer defects in the elastic semipermeable membrane 105 that is applied thereon.

Insertion Device Recessed Push Rod

As described above, in some embodiments, the sinus dilator includes an elongated proximal end. In these embodiments, the insertion device may be configured to have a shape and size compatible with the elongated proximal anchor of the sinus dilator. In some instances, the insertion device is configured such that the sinus dilator can be removably mounted at the distal end of the insertion device. In certain cases, the hollow elongated member of the insertion device has a distal end sized such that at least a portion of the elongated proximal end of the device fits inside the distal end of the hollow elongated member of the insertion device. In some instances, the interior elongated member of the insertion device is recessed within the hollow elongated member to accommodate the elongated proximal end of the sinus dilator in the hollow elongated member of the insertion device.

During use, the actuation of the trigger may cause the interior elongated member to displace such that at least a portion of the interior elongated member that is inside of the distal end of the hollow elongated member is displaced distally within the hollow elongated member. In some instances, the distal tip of the interior elongated member may push against the sinus dilator as the interior elongated member is displaced distally within the hollow elongated member. As such, in some instances, the interior elongated member is relatively displaceable with respect to the hollow elongated member such that upon actuation of the trigger, the interior elongated member is displaced distally within the hollow elongated member. In certain instances, the trigger is slidably coupled to the handle and the trigger is coupled to the interior elongated member such that sliding the trigger relative to the handle displaces the interior elongated member distally relative to the hollow elongated member.

In certain embodiments, the distal end of the interior elongated member is configured to mate with the proximal anchor of the sinus dilator. For example, the distal end of the interior elongated member of the insertion device may include one or more slots configured to mate with the one or more radially outward extending members of the proximal anchor described above. In some cases, at least a portion of each radially outward extending member of the proximal anchor is configured to fit within a corresponding slot at the distal end of the interior elongated member of the insertion device. In some embodiments, mating the proximal anchor to the distal end of the interior elongated member of the insertion device facilitates inserting the sinus dilator into the sinus ostium by minimizing undesired rotation of the sinus dilator about its longitudinal axis as the sinus dilator is inserted into the sinus ostium using the insertion device.

Aspects of the insertion device include a handheld member including a handle and trigger and a hollow elongated member having a proximal end coupled to the handheld member and a distal end having an opening to an interior cavity of the hollow elongated member. The hollow elongated member includes a retention interface configured to removably couple to a proximal end of a sinus dilator. The insertion device includes an interior elongated member extending within the interior cavity of the hollow elongated member. A distal end of the interior elongated member is recessed from the distal end of the hollow elongated member a distance sufficient to accommodate insertion of the proximal end of the sinus dilator.

Insertion Device Distal Tip Angle

Aspects of certain embodiments include an insertion device for inserting a sinus dilator into a stenotic opening of a maxillary sinus of a patient. The device includes a handheld member, including a handle and trigger, and a hollow elongated member having a proximal end coupled to the handheld member and a distal end having a retention interface for removably coupling to the sinus dilator. The hollow elongated member has a middle section extending between the distal and proximal ends, the middle section having an axis. The device includes an interior elongated member extending within the interior cavity of the hollow elongated member.

In certain embodiments, the distal end of the hollow elongated member is oriented at an angle of 0° to 150° relative to the axis, such as 10° to 130°, including 20° to 120°, or 30° to 120°, or 60° to 120°, or 90° to 120°, or 100° to 120°, or 105° to 115° relative to the axis. In some instances, the distal end of the hollow elongated member is oriented at an angle of 110° relative to the axis. In certain embodiments, an insertion device having a distal end with an angle as described above may facilitate insertion of a sinus dilator into a maxillary sinus of a patient.

In accordance with another aspect, and as shown in FIG. 9, the dilator 100 has a bend 206 at the distal end thereof. The degree of bend 206 can be measured as the angle $\theta$ that is formed between the axis of the middle portion of cannula 201 and the axis of dilator 100. In certain embodiments of insertion device that are particularly well adapted for accessing the maxillary sinus opening 11, the angle $\theta$ ranges from 105° to 115°. In other embodiments, the angle $\theta$ is 110°.

As can be appreciated from the disclosure provided above, the present disclosure has a wide variety of applications. Accordingly, the following examples are offered for illustration purposes and are not intended to be construed as a limitation on the invention in any way. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

Example 1

A distal osmotic tablet was fabricated according to the procedures described in Example 1 of U.S. patent application Ser. No. 13/219,505, filed Aug. 26, 2011, except as follows. First, Polyox 303 was sifted through a 100-mesh sieve. 8.5 grams of minus 100 mesh material was transferred to a beaker. Sodium chloride powder was ground with a pestle in a mortar and sifted through a 100-mesh sieve. 15.0 grams of sized sodium chloride was added to the Polyox. Next, Methocel E5 was sifted through a 100-mesh sieve. 1.25 g of the sized Methocel was added to the Polyox and sodium chloride. The resulting composition was stirred with a spatula to form a homogenous blend. 7 ml of denatured anhydrous ethanol (formula 3A) was slowly stirred into the blend to form a homogenous damp mass. The mass was passed through a 40 mesh sieve with a spatula to form granules. The resulting granules were transferred to a beaker and dried overnight in forced air at 40° C. The dried granules were then sized again through the 40 mesh sieve and transferred to a screw-capped jar. An amount of magnesium stearate equal to 1 percent of the mass of the dried composition was weighed, sized through an 80-mesh sieve, and tumble mixed into the blend for two minutes. Portions of the resulting granulation having a nominal weight of 19.5 mg were compacted into annular shaped tablets using 60 pounds force with flat-faced beveled round tooling having an outside diameter of 2.7 mm and an inside diameter of 0.92 mm. This produced osmotic distal tablets having a nominal length of 2.5 mm. The nominal weight of sodium chloride in the distal tablets was 11.7 mg.

A proximal osmotic tablet composition was prepared using the same procedures and compositions except that the mass of Polyox was 10.98 g and the mass of sodium chloride was 12.5 grams. Additionally, 30 mg of red ferric oxide pigment, previously sized to minus 100 mesh, was included in the blend during the wet granulation step. The resulting granulation was compacted with the 2.7 mm outside diameter 0.92 mm inside diameter tooling at a nominal weight of 18.6 mg to produce proximal osmotic tablets having a nominal length of 2.5 mm. The nominal sodium chloride in the proximal tablets was 9.3 mg.

Next, stainless steel tubes of 304 stainless steel having an outside diameter of 28 mils (0.7 mm) and an inside diameter of 20 mils (0.5 mm) were cut to lengths of 55 mm, de-burred and passivated using the procedures described in Example 1 U.S. patent application Ser. No. 13/219,505, filed Aug. 26, 2011. The tubes were then dip coated using the procedures described in Example 1 U.S. patent application Ser. No. 13/219,505, filed Aug. 26, 2011, using a coating solution comprising 11.7 parts Tecophilic HP93A-100, 1.3 parts polyvinyl pyrrolidone, and 87 parts n-methyl pyrrolidone and dried to a coating thickness of 3-4 mils (0.076-0.102 mm). Then, one proximal tablet and one distal tablet were threaded onto the center of a coated tube such that they were in contact with each other. The resulting subassembly was then dip coated with the same membrane coating solution using the procedures described in Example 1 U.S. patent application Ser. No. 13/219,505, filed Aug. 26, 2011, and dried to a nominal coating thickness on the osmotic tablets of 13 mils (0.3 mm).

Next, excess membrane material was trimmed away from the stainless steel tube using a jeweler's lathe such that 2 mm of membrane remained at each end of the pair of tablets. The metal tube was then cut such that 4.2 mm of bare metal tube remained on the proximal end and 1.7 mm of bare metal tube remained on the distal end. A proximal anchor comprising injection molded Pebax having two wings and a shape substantially as shown in FIGS. 3 and 4 was slipped onto the proximal end abutting the trimmed membrane. An extruded sleeve of Nylon 12 tubing having an inside dimension of approximately 31 mils (0.8 mm), an outside diameter of 70 mils (1.8 mm), and a length of about 50 mils (1.3 mm) was then bonded onto the bare stainless steel tubing of the proximal end using Loctite 4011 cyanoacrylate adhesive and dried at room temperature for 2 days. Next, a distal tip that had been injection molded from Nylon 66 was fitted onto the distal end of the tube abutting the trimmed membrane and adhered with Loctite 4011. The tip had a conical configuration with the wide end of the cone abutting the membrane. Dimensions of the conical tip were approximately 80 mils (2 mm) tapering down to approximately 45 mils (1.1 mm) over a length of approximately 50 mils (1.3 mm). The conical tip had a central hole running lengthwise having an inside diameter of approximately 32 mils (0.8 mm).

The resulting dilator was tested in a USP paddle test with 500 ml of distilled water at a temperature of 37° C. using a paddle rotation speed of 50 revolutions per minute. The device expanded over duration of 1 hour. The proximal tablet expanded during that period from 3.4 mm to 5.3 mm while the distal tablet expanded from 3.4 mm to 5.4 mm to form the tapered configuration of an in situ osmotic anchor.

The preceding merely illustrates the principles of the disclosure. All statements herein reciting principles, aspects, and embodiments of the disclosure as well as specific examples thereof, are intended to encompass both structural and functional equivalents thereof. Additionally, it is intended that such equivalents include both currently known equivalents and equivalents developed in the future, e.g., any elements developed that perform the same function, regardless of structure. The scope of the present disclosure, therefore, is not intended to be limited to the exemplary embodiments shown and described herein. Rather, the scope and spirit of present disclosure is embodied by the appended claims.

What is claimed is:

1. A device for dilating a stenotic opening of a maxillary sinus in a subject, the device comprising:
   (a) a self-expanding osmotic driver configured to expand an expandable portion from a non-expanded configuration to an expanded configuration, the osmotic driver comprising a first osmotic driver and a second osmotic driver positioned distally to the first driver; and
   (b) the expandable portion disposed peripherally around the first and second osmotic drivers and configured to expand from the non-expanded configuration to the expanded configuration, wherein the non-expanded configuration is sized to be positioned within the stenotic opening;
   wherein the second driver is configured to have (i) a faster rate of expansion than a rate of expansion of the first driver, and (ii) a duration of expansion less than a duration of expansion of the first driver, whereby the second driver is configured to prevent the device from being expelled from the stenotic opening and into the nasal cavity during device expansion.

2. The device of claim 1, wherein the second driver is configured to have a duration of expansion of 2 hours or less.

3. The device of claim 1, wherein each of the first and second drivers comprises an osmotically active agent, the second osmotic driver having a concentration of the agent greater than the concentration of the agent in the first driver.

4. The device of claim 3, wherein the osmotically active agent in the second driver has a concentration of 45 to 75 wt % and the osmotically active agent in the first driver has a concentration of 35 to 65 wt %.

5. The device of claim 1, wherein each of the first and second drivers comprises an osmopolymer, the second driver having a concentration of the osmopolymer that is less than the concentration of the osmopolymer in the first driver.

6. The device of claim 5, wherein the osmopolymer in the first driver has a concentration of 30 to 60 wt % and the osmopolymer in the second driver has a concentration of 20 to 50 wt %.

7. The device of claim 1, wherein the second driver is configured to have a diameter greater than the diameter of the first driver during a period of stenotic opening dilation; and the second driver is configured to have a diameter less than the diameter of the first driver following said period of stenotic opening dilation.

8. The device of claim 1, wherein the period of stenotic opening dilation is 0.5 hours or more.

9. The device of claim 7, wherein the period of stenotic opening dilation is 2 hours or less.

10. The device of claim 1, comprising a conduit defining an interior lumen, wherein the conduit comprises a distal end configured to be in fluid communication with an interior cavity of the maxillary sinus in the subject and a proximal end configured to be in fluid communication with a nasal cavity in the subject, and wherein the conduit is configured to allow fluid flow between the interior cavity of the maxillary sinus and the nasal cavity when the device is positioned within the stenotic opening.

11. The device of claim 1, wherein the expandable portion comprises a semipermeable membrane.

12. The device of claim 1, comprising a proximal anchor proximate to the proximal end of the device, wherein the proximal anchor is configured to prevent the device from moving into a maxillary sinus cavity of the subject during device expansion.

* * * * *